US009765009B2

(12) United States Patent
Burdeniuc et al.

(10) Patent No.: US 9,765,009 B2
(45) Date of Patent: *Sep. 19, 2017

(54) PROCESSES, PRODUCTS, AND COMPOSITIONS HAVING TETRAALKYLGUANIDINE SALT OF AROMATIC CARBOXYLIC ACID (71) Applicant: EVONIK DEGUSSA GMBH, Essen (DE)

(72) Inventors: Juan Jesus Burdeniuc, Colmar, PA (US); Matti Sakari Huhtasaari, Hamburg (DE)

(73) Assignee: Evonik Degussa GmbH, Essen (DE)

( * ) Notice: Subject to any disclaimer, the term of this patent is extended or adjusted under 35 U.S.C. 154(b) by 250 days.

This patent is subject to a terminal disclaimer.

(21) Appl. No.: 13/678,736

(22) Filed: Nov. 16, 2012

(65) Prior Publication Data
US 2013/0131276 A1 May 23, 2013

Related U.S. Application Data (60) Provisional application No. 61/560,892, filed on Nov. 17, 2011.

(51) Int. Cl.
| *C07C 63/20* | (2006.01) |
| *C08G 18/08* | (2006.01) |
| *C08G 65/00* | (2006.01) |
| *C08G 18/48* | (2006.01) |
| *C08G 18/54* | (2006.01) |
| *C08G 18/63* | (2006.01) |
| *C08G 18/66* | (2006.01) |
| *C08G 18/76* | (2006.01) |
| *C08G 18/18* | (2006.01) |
| *C08G 18/32* | (2006.01) |
| *C08G 18/40* | (2006.01) |
| *C08G 18/42* | (2006.01) |
| *C08G 101/00* | (2006.01) |

(52) U.S. Cl.
CPC ............. *C07C 63/20* (2013.01); *C08G 18/08* (2013.01); *C08G 18/1858* (2013.01); *C08G 18/1875* (2013.01); *C08G 18/3206* (2013.01); *C08G 18/3275* (2013.01); *C08G 18/4072* (2013.01); *C08G 18/42* (2013.01); *C08G 18/4841* (2013.01); *C08G 18/546* (2013.01); *C08G 18/632* (2013.01); *C08G 18/6674* (2013.01); *C08G 18/6688* (2013.01); *C08G 18/7621* (2013.01); *C08G 18/7671* (2013.01); *C08G 65/00* (2013.01); *C08G 2101/0008* (2013.01); *C08G 2101/0025* (2013.01); *C08G 2101/0083* (2013.01)

(58) Field of Classification Search
CPC .......................... C08G 2101/0025; C07C 63/20
USPC ........ 502/167; 521/170, 172, 173, 174, 128, 521/129, 164, 167
See application file for complete search history.

(56) References Cited

U.S. PATENT DOCUMENTS

| 3,280,214 | A | | 10/1966 | Mitchell |
| 3,391,113 | A | | 7/1968 | Lopez et al. |
| 3,663,258 | A | | 5/1972 | Wiese, Jr. et al. |
| 4,025,466 | A | | 5/1977 | Jourquin et al. |
| 4,191,815 | A | | 3/1980 | Jourquin et al. |
| 4,200,571 | A | | 4/1980 | Wolfe |
| 4,394,491 | A | | 7/1983 | Hoffman |
| 4,525,470 | A | * | 6/1985 | Kohl ............................. 502/167 |
| 5,304,578 | A | * | 4/1994 | Tamano et al. ................. 521/51 |
| 5,322,914 | A | | 6/1994 | McInnis et al. |
| 7,700,533 | B2 | | 4/2010 | Egbe et al. |
| 8,372,935 | B2 | | 2/2013 | Maliverney et al. |
| 2007/0287761 | A1* | | 12/2007 | Bender et al. ................. 521/129 |
| 2009/0300946 | A1 | | 12/2009 | Egbers et al. |
| 2010/0249260 | A1* | | 9/2010 | Casati et al. .................. 521/170 |

FOREIGN PATENT DOCUMENTS

| CN | 101998960 A | 3/2011 |
| EP | 0 559 216 A1 | 9/1993 |
| JP | 02-003487 | 1/1990 |
| JP | 05306318 | 11/1993 |
| JP | 07216295 A | 8/1995 |
| JP | 8-213286 A | 8/1996 |

(Continued)

OTHER PUBLICATIONS

Casati, F.M., et al.; "Influence of Non-Fugitive Catalysis on Physical Characteristics of Automotive Polyurethane Molded Foam".
Bonner, O.D.; "Unusual Ion Pairs and Their Relationship to Acid Ionization"; Journal of Solution Chemistry; vol. 9, No. 11; Nov. 1980; pp. 877-884.
Chantooni, M.K., et al.; "Comparison of Substituent Effects on Dissociation and Conjugation of Phenols with those of Carboxylic Acids in Acetonitrile, N,N-Dimethylformamide, and Dimethyl Sulfoxide"; The Journal of Physical Chemistry; vol. 80, No. 12; Jun. 1, 1976; pp. 1306-1310.
Yijun Liu, Chemical Industry Press, Handbook of Raw Materials and Additives for Polyurethanes, the 1st Edition, pp. 211-214, (Jan. 2015).

*Primary Examiner* — John Cooney
(74) *Attorney, Agent, or Firm* — Andrew H. Chung; Linda S. Li; Jason S. Ngui (57) ABSTRACT Disclosed are processes, products, and compositions having tetraalkylguanidine salt of aromatic acid. The processes include providing a pre-mix comprising an aromatic carboxylic acid component and contacting a tetraalkylguanidine with the aromatic carboxylic acid component in the pre-mix to form the tetraalkylguanidine salt of aromatic carboxylic acid or producing a catalyst composition by contacting the tetraalkylguanidine with the aromatic carboxylic acid component to form the tetraalkylguanidine salt of aromatic carboxylic acid. The compositions include the tetraalkylguanidine salt of aromatic carboxylic acid. The product is formed by the tetraalkylguanidine salt of aromatic carboxylic acid.

27 Claims, 4 Drawing Sheets

(56) References Cited

FOREIGN PATENT DOCUMENTS

| WO | 01/58976 A1 | 8/2001 |
|---|---|---|
| WO | 03/016372 A1 | 2/2003 |
| WO | 03/016373 A1 | 2/2003 |
| WO | 03/055930 A1 | 7/2003 |
| WO | 2004/060956 A1 | 7/2004 |
| WO | 2006/116456 A1 | 11/2006 |

* cited by examiner

PROCESSES, PRODUCTS, AND COMPOSITIONS HAVING TETRAALKYLGUANIDINE SALT OF AROMATIC CARBOXYLIC ACID

CROSS-REFERENCE TO RELATED APPLICATIONS

This application claims the benefit of U.S. Application No. 61/560,892, filed on Nov. 17, 2011. The disclosure of Application No. 61/560,892 is hereby incorporated by reference.

BACKGROUND OF THE INVENTION

The present invention is directed to processes, compositions, and products having tetraalkylguanidine salt of aromatic carboxylic acid. In addition, the present invention relates to polyurethane processes, compositions, products, and catalysts.

Known polyurethane products are made from tetraalkylguanidine salts made from formic acid, acetic acid, octanoic acid, 2-thylhexanoic acid, or other acids lacking aromaticity in their chemical structure. Such salts can require high temperatures for curing polyurethane products. Such cure inhibition can be desirable at the front end of a cure process by maintaining a lower viscosity and providing an opportunity for a mold to be filled when a polyurethane composition is being poured into it. However, such inhibition can be undesirable at the back end of the cure process because it can result in uncured portions, inconsistently cured portions, or inconsistent physical properties.

U.S. Pat. No. 3,280,214, which is hereby incorporated by reference in its entirety, describes an organopolysiloxane copolymer and a method for the organopolysiloxane copolymer. The method includes a single step of producing a wide range of specific block copolymers of organopolysiloxanes. Specifically, the method uses tetramethylguanidine octoate to cure a block copolymer and produce a material with good adhesion to aluminum. The tetramethylguanidine octoate is an aliphatic salt and suffers from a drawback that is temperature dependent when used in curing of elastomeric polyurethane polymers.

U.S. Pat. No. 3,663,258, which is hereby incorporated by reference in its entirety, describes a coating composition containing a dye and tetramethylguanidine trichloroacetate in a solution of inert binder at a pH not higher than 3. The acidic solution of tetramethylguanidinium trichloroacetate is dissolved in the minimum amount of water and the solution is added to a solution of the dye and binder in a water miscible organic solvent. The acid is a non-aromatic acid and suffers from a drawback that it requires the use of excess acid.

U.S. Pat. No. 3,391,113, which is hereby incorporated by reference in its entirety, describes thermosettable resin mixtures that include epoxy resin having a plurality of 1,2-epoxy groups. Tetraalkylguanidines are used to accelerate cure of dicyanamide-epoxy resin mixtures in powder form, prepared by grinding together dicyanamide and tetraalkylguanidine. The process suffers from a drawback that it requires grinding of solids and the composition requires dicyanamide to accelerate the cure of the epoxy resin.

U.S. Pat. No. 4,025,466, which is hereby incorporated by reference in its entirety, describes a process for preparing polyurethane foam. The process includes reacting a polyisocyanate and a polyol in the presence of a catalyst containing the chemical structure =N—C=N— and a metal salt carboxylate. Tetramethylguanidine is used as a catalyst to make polyurethane foam together with carboxylate salts such as sodium formate and potassium acetate. The process suffer from a drawback that formate salts and/or acetate salts would product foam with poor physical properties, can result in extensive deterioration, can lead to defective products, and/or can be too reactive for certain applications.

A process, a polyurethane composition, a polyurethane product, a process of producing a catalyst composition, and a catalyst that do not suffer from one or more of the above drawbacks would be desirable in the art.

BRIEF SUMMARY OF THE INVENTION

The instant invention can solve problems associated with conventional materials and processes by providing a tetraalkylguanidine salt of aromatic carboxylic acid. The inventive salts can be used to produce a wide range of polyurethane compounds including flexible foams, spray foams (e.g., non-emissive insulating foams), and elastomeric.

In an exemplary embodiment, a process includes providing a pre-mix comprising an aromatic carboxylic acid component and contacting a tetraalkylguanidine with the aromatic carboxylic acid component in the pre-mix to form a tetraalkylguanidine salt of aromatic carboxylic acid.

In another exemplary embodiment, a polyurethane composition includes a polyol component, a catalyst composition, and an isocyanate component. The catalyst composition includes tetraalkylguanidine salt of aromatic carboxylic acid.

In another exemplary embodiment, a polyurethane product includes being formed by a tetraalkylguanidine salt of aromatic carboxylic acid and an isocyanate component.

In another exemplary embodiment, a process of producing a catalyst composition includes contacting a tetraalkylguanidine with an aromatic carboxylic acid component to form a tetraalkylguanidine salt of aromatic carboxylic acid.

In another exemplary embodiment, a catalyst includes a tetraalkylguanidine salt of aromatic carboxylic acid.

In a further exemplary embodiment, a catalyst which is free or substantially free of mercury and mercury containing compounds is provided.

In a further exemplary embodiment, a catalyst which is free or substantially free of tin and tin containing compounds is provided.

In a further exemplary embodiment, a catalyst which is free or substantially free of heavy metals (Pb, Bi, Sb, Mn, Fe, Ti, La, Zr, Zn, Co) and heavy metals containing compounds is provided.

Other features and advantages of the present invention will be apparent from the following more detailed description of the preferred embodiment, taken in conjunction with the accompanying drawings which illustrate, by way of example, the principles of the invention. These features can be used alone or in combination with each other.

BRIEF DESCRIPTION OF SEVERAL VIEWS OF THE DRAWINGS

Wherever possible, the same reference numbers will be used throughout the drawings to represent the same parts.

DETAILED DESCRIPTION OF THE INVENTION

The instant invention relates to a process, a polyurethane composition, a polyurethane product, a process of producing a catalyst composition, and a catalyst. Embodiments of the present disclosure decrease temperature dependence of curing, permit more consistent curing, increase physical properties of cured products, permit viscosity of poured polyurethane to be lower at the front end of curing while higher at the back end of curing, permit formation of microcellular foams such as in shoe soles and foamed sealants by providing longer cream time and better curing, can reduce scrap rates, can increase productivity, can permit better flow, and combinations thereof. While the embodiments of the present disclosure can be used in combination with mercury or other heavy metals (Sn, Pb, Bi, Sb, Mn, Fe, Ti, La, Zr, Zn, Co) and mercury or other heavy metals (Sn, Pb, Bi, Sb, Mn, Fe, Ti, La, Zr, Zn, Co) containing compounds, the embodiments of the present disclosure can also be free or substantially free of mercury and other heavy metals (Sn, Pb, Bi, Sb, Mn, Fe, Ti, La, Zr, Zn, Co) and mercury and other heavy metals (Sn, Pb, Bi, Sb, Mn, Fe, Ti, La, Zr, Zn, Co) containing compounds. By "substantially free" of mercury and other heavy metals (Sn, Pb, Bi, Sb, Mn, Fe, Ti, La, Zr, Zn, Co) and mercury and other heavy metals (Sn, Pb, Bi, Sb, Mn, Fe, Ti, La, Zr, Zn, Co) containing compounds, it is meant that the catalyst as well as the other components that are used to form a polyurethane product contain less than about 1.0 pphp and typically less than about 0.1 pphp and, if desired about 0% mercury and other heavy metals (Sn, Pb, Bi, Sb, Mn, Fe, Ti, La, Zr, Zn, Co) and mercury or other heavy metals (Sn, Pb, Bi, Sb, Mn, Fe, Ti, La, Zr, Zn, Co) containing compounds.

The catalyst composition of the instant invention relates comprises a tetraalkylguanidine salt of aromatic carboxylic acid. The salt has a structure of: $\_[HN=C(NR^1{}_2)_2]_Z\{(R^2)_x(R^3)_y(Ar)[(CH_2)_n(CO_2H)]_z\}$ wherein $R^1$ is independently C1-12 alkyl; $R^2=H$; $R^3=C_{1-4}$ alkyl, OH, $-CO_2-R^4$ or $-CONHR^4$ or $-CO2M$ wherein $R^4=C_{1-4}$ alkyl, $-(C_2H_4O)_m-H$ wherein m=1 to 10 and M=Li, Na, K; Ar=substituted $C_6$ (Phenyl) or $C_{10}$ (Naphtalenic) ring; n=0 to 6; x=0-5 and y=0-5 and z=1-3 for a C6 aromatic ring or x=0-9 and y=0-9 and z=1-3 for a C10 aromatic naphthalenic ring.

In the above formula it is preferred that $R^1$=Methyl; $R^2$=H; $R^3$=CH3, OH or $-CO_2-R^4$ wherein $R^4=-(C_2H_4O)_m-H$ wherein m=1 to 5; z=1; x=4-5; y=0-1; n=0; Ar=substituted $C_6$ (Phenyl).

The salt can be produced by contacting a tetraalkylguanidine having a structure of: $[HN=C(NR1_2)_2]-$ wherein $R^1$ is independently $C_{1-12}$ alkyl, with an aromatic carboxylic acid having a structure of $\{(R^2)_x(R^3)_y(Ar)[(CH_2)_n(CO_2H)]_z\}-$ wherein $R^2$=H; $R^3=C_{1-4}$ alkyl, OH, $-CO_2-R^4$ or $-CONHR^4$ or $-CO2M$ wherein $R^4=C_{1-4}$ alkyl, $-(C_2H_4O)_m-H$ wherein m=1 to 10 and M=Li, Na, K; Ar=substituted $C_6$ (Phenyl) or $C_{10}$ (Naphtalenic) ring; n=0 to 6; x=0-5 and y=0-5 and z=1-3 for a C6 aromatic ring or x=0-9 and y=0-9 and z=1-3 for a C10 aromatic naphthalenic ring.

The salt is typically produced by mixing in a suitable solvent or in the absence of a solvent the aromatic carboxylic acid with a tetralkylguanidine compound in a ratio such that all the acidity is neutralized by the tetralkylguanidine compound. Suitable solvents and diluents include ethylene glycol, diethylene glycol, polyethylene glycol or various molecular weights (MW=150-300) such as PEG-200, MP-diol, propylene glycol, dipropylene glycol, polypropylene glycol and water. The molar ratio of tetraalkylguandine to carboxylic acid groups in the aromatic carboxylic acid typically ranges from about 0.7 to about 1.3.

Figure 1:
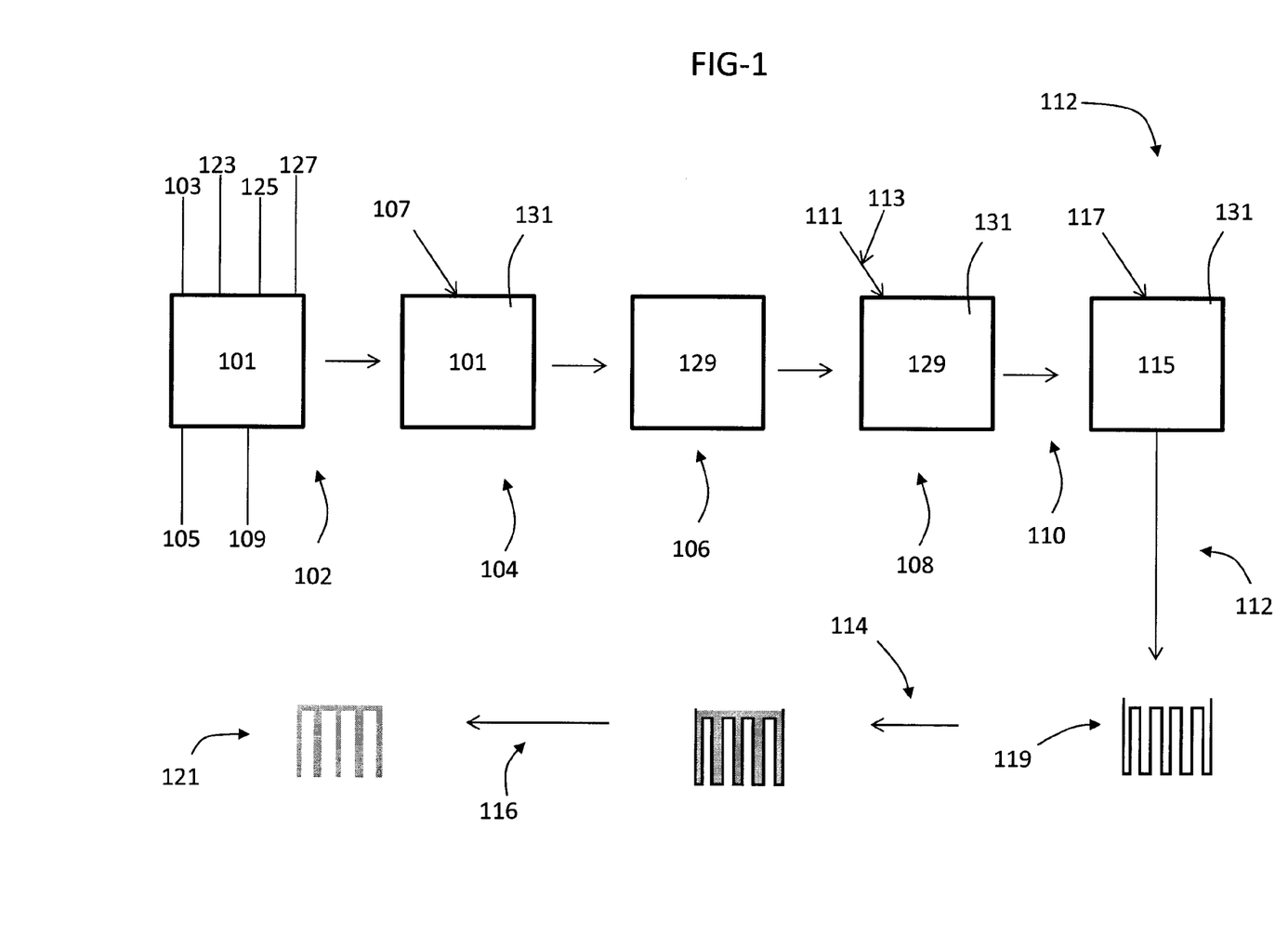
FIG. 1 is a schematic view of an exemplary process according to the disclosure.

Referring to FIG. 1, in one embodiment, a process 100 of producing a composition includes providing a pre-mix 101 (step 102). The pre-mix 101 includes an aromatic carboxylic acid component 103 (for example, benzoic acid, phthalic acid, phenyl-propionic acid, salicylic acid, or combinations thereof). The pre-mix 101 includes a solvent (for example, if the aromatic carboxylic acid component 103 is used for forming a solid or semi-solid product) or a polyol component 109 without the solvent (for example, if the aromatic carboxylic acid component 103 is used for forming a liquid product). Examples of solvents include ethylene glycol, diethylene glycol, polyethylene glycol or various molecular weights (MW=150-300) such as PEG-200, MP-diol, propylene glycol, dipropylene glycol, polypropylene glycol and water. The amount of solvent typically ranges from about 0% to about 90%. In one embodiment, the aromatic carboxylic acid component 103 includes a phenyl group or a substituted phenyl group.

In one embodiment, the pre-mix 101 includes the polyol component 109, a surfactant component 123, a blowing agent component 125, and a crosslinking component 127. The polyols component 109 includes one or more standard polyols, one or more copolymer polyols, one or more natural oil polyols, or combinations thereof. In one embodiment, the standard polyol is used alone, includes polyether polyol, and/or is at an amount about 10 pphp to about 100 pphp. In one embodiment, the copolymer polyol is at an amount of about 0 to about 80 pphp. In one embodiment, the natural oil polyol is at an amount of about 0 to about 40 pphp. In one embodiment, the pre-mix 101 includes about 55 parts per one hundred parts polyol (pphp) of a first polyol (for example, a high functionality capped polyether polyol and/or high molecular weight functionality having a molecular weight of about 5,000) in the polyol component 109, about 45 pphp of a second polyol (for example, a grafted polyether polyol containing copolymerized styrene and acrylonitrile and having a molecular weight of about 4,800) in the polyol component 109, about 3.0 pphp water, about 0.60 pphp surfactant (for example, a silicon surfactant) in the surfactant component 123, about 0.70 pphp crosslinking agent (for example, diethanolamine) in the crosslinking component 127, or combinations thereof.

Suitable cell stabilizers components include at least one member selected from the group consisting of silicone surfactants as well as organic anionic, cationic, zwitterionic or nonionic surfactants. Examples of suitable silicone surfactants include, but are not limited to, polyalkylsiloxanes, polyoxyalkylene polyol-modified dimethylpolysiloxanes, alkylene glycol-modified dimethylpolysiloxanes, or any combination thereof. Suitable anionic surfactants include, but are not limited to, salts of fatty acids, salts of sulfuric acid esters, salts of phosphoric acid esters, salts of sulfonic acids, and combinations of any of these. Suitable cationic surfactants include, but are not limited to quaternary ammonium salts (pH dependent or permanently charged) such as cetyl trimethylammonium chloride, cetyl pyridinium chloride, polyethoxylated tallow amine, benzalkonium chloride, benzethonium chloride and the like. Suitable zwitterionic or amphoteric surfactants include but are not limited to sultaines, aminoacids, imino acids, betaines and phosphates. Suitable non-ionic surfactants include but are not limited to fatty alcohols, polyoxyethylene glycol alkyl ethers, polyoxypropylene glycol alkyl ethers, glucosides (such as decyl, lauryl and octyl glucosides), polyoxyethylene glycol alkyl phenol ethers, glycol alkyl esters, and the like.

The amount of surfactant typically ranges from about 0.1 pphp to about 10 pphp.

Suitable blowing agent components includes at least one member selected from the group consisting of compounds with low boiling points which are vaporized during the exothermic polymerization reaction. Such blowing agents are generally inert or they have low reactivity and therefore it is likely that they will not decompose or react during the polymerization reaction. Examples of low reactivity blowing agents include, but are not limited to, carbon dioxide, chlorofluorocarbons (CFCs), hydrofluorocarbons (HFCs), hydrochlorofluorocarbons (HCFCs), fluoroolefins (FOs), chlorofluoroolefins (CFOs), hydrofluoroolefins (HFOs), hydrochlorfluoroolefins (HCFOs), acetone, and low-boiling hydrocarbons such as cyclopentane, isopentane, n-pentane, and their mixtures. Other suitable blowing agents include compounds, for example water, that react with isocyanate compounds to produce a gas. The amount of blowing agent typically ranges from about 0 (water blown) to about 80 pphp. Water (blow foam by reacting with isocyanate making $CO_2$) can be present in the range from about 0 (if a BA is included) to about 60 pphp (a very low density foam) and typically from about 1.0 pphp to about 10 pphp and, in some cases, from about 2.0 pphp to about 5 pphp.

Suitable crosslinking agents (forming a portion of or all of the crosslinking component 127) include, but are not limited to, low-molecular weight compounds containing at least two moieties, such as, hydroxyl groups, primary amino groups, secondary amino groups, other active hydrogen-containing groups that are reactive with an isocyanate group, or combinations thereof. In one embodiment, the crosslinking agent is a polyhydric alcohol (for example, a trihydric alcohol, such as, glycerol or trimethylolpropane), a polyamine, or a combination thereof. In one embodiment with the crosslinking agent being a polyamine, the crosslinking agent is diethyltoluenediamine, chlorodiaminobenzene, diethanolamine, diisopropanolamine, triethanolamine, tripropanolamine, 1,6-hexanediamine, or combinations thereof. In one embodiment with the crosslinking agent being a diamine, the crosslinking agent includes twelve or fewer carbon atoms, seven carbon atoms, or less than seven carbon atoms. The amount of crosslinking agents typically ranges from about 0.1 pphp to about 20 pphp In one embodiment, the pre-mix 101 further includes water, cell stabilizers, chain extenders, pigments, fillers, flame retardants, auxiliary urethane gelling catalysts, auxiliary urethane blowing catalysts, transition metal catalysts, or combinations thereof. As is further described below, in some embodiments, the pre-mix 101 includes further components that are added through any suitable procedures and/or at any suitable portion of the process 100, for example, as part of an intermediate mix 129, described below. In one embodiment, the catalyst composition 111 is added to the pre-mix 101 to form the intermediate mix 129 and an isocyanate component 117 is added to form a polyurethane composition 115.

Suitable cell stabilizers include, but are not limited to, silicone surfactants, anionic surfactants, or combinations thereof. In one embodiment, the cell stabilizer is the silicone surfactant, such as, polyalkylsiloxane, polyoxyalkylene polyol-modified dimethylpolysiloxane, alkylene glycol-modified dimethylpolysiloxane, or combinations thereof. In one embodiment, the cell stabilizer is the anionic surfactant, such as, a salt of a fatty acid, a salt of a sulfuric acid ester, a salt of a phosphoric acid ester, a salt of a sulfonic acid, or a combination thereof. In one embodiment, the pre-mix 101, the intermediate mix 129, and/or the polyurethane composition 115 include the cell stabilizers at a suitable predetermined amount. Suitable predetermined amounts include, but are not limited to, about 0.1 pphp to about 20 pphp, 0.1 pphp to about 10 pphp, 0.1 pphp to about 5 pphp, or any suitable combination or sub-combination thereof.

Suitable chain extenders include, but are not limited to, compounds having a hydroxyl or amino functional group, such as, glycols, amines, diols, water, or combinations thereof. In one embodiment, the chain extender is ethylene glycol, diethylene glycol, propylene glycol, dipropylene glycol, 1,4-butanediol, 1,3-butanediol, 1,5-pentanediol, neopentyl glycol, 1,6-hexanediol, 1,10-decanediol, 1,12-dodecanediol, ethoxylated hydroquinone, 1,4-cyclohexanediol, N-methylethanolamine, N-methylisopropanolamine, 4-aminocyclohexanol, 1,2-diaminothane, 2,4-toluenediamine, or combinations thereof. The amount of chain extenders typically ranges from about 0 pphp to about 20 pphp.

Suitable pigments include, but are not limited to, organic pigments, inorganic pigments, or combinations thereof. The pigments permit coloring (for example, to match a color grade), concealing (for example, to conceal yellowing), or combinations thereof. In one embodiment with the pigment being an organic pigment, the pigment is an azo/diazo dye, a phthalocyanine, dioxazine, carbon black, or combination thereof. In one embodiment with the pigment being an inorganic pigment, the pigment is titanium dioxide, iron oxide, chromium oxide, or a combination thereof. The amount of pigments typically ranges from about 0 pphp to about 10 pphp.

Suitable fillers increase the density and load bearing properties of polyurethane foams. In one embodiment, the filler is barium sulfate, calcium carbonate, or a combination thereof. The amount of fillers typically ranges from about 0 pphp to about 40 pphp.

Suitable flame retardants reduce the flammability of polyurethane foams. In one embodiment, the flame retardant is a chlorinated phosphate ester, a chlorinated paraffin, a melamine powder, or a combination thereof. In one embodiment, the pre-mix 101, the intermediate mix 129, and/or the polyurethane composition 115 include the flame retardants at a suitable amount. Suitable amounts include, but are not limited to, about 0 pphp to about 20 pphp, about 0 pphp to about 10 pphp, about 0 pphp to about 5 pphp, about 1 pphp to about 20 pphp, about 1 pphp to about 10 pphp, about 1 pphp to about 5 pphp, or any suitable combination or sub-combination thereof.

Suitable auxiliary urethane gel catalyst, auxiliary urethane blowing catalysts and transition metal catalyst comprise at least one member selected from the group consisting of tertiary amine catalysts that contain an isocyanate-reactive group or not. Isocyanate reactive groups comprise primary amine, secondary amine, hydroxyl group, amide or urea. Tertiary amine catalysts containing isocyanate reactive groups include both gelling and blowing catalysts. Exemplary gelling catalysts include N,N-bis(3-dimethylaminopropyl) N-isopropanolamine; N,N-dimethylaminoethyl-N'-methyl ethanolamine (DABCO® T, Air Products and Chemicals, Inc. of Allentown, Pa.); N,N,N'-trimethylaminopropyl ethanolamine (POLYCAT® 17, by Air Products and Chemicals, Inc.), N,N-dimethylethanolamine (DABCO® DMEA); N,N-dimethyl-N',N'-2-hydroxy(propyl)-1,3-propylenediamine; dimethylaminopropylamine (DMAPA); (N,N-dimethylaminoethoxy)ethanol, methyl-hydroxy-ethyl-piperazine, bis(N,N-dimethyl-3-aminopropyl)amine (POLYCAT® 15), N,N-dimethylaminopropyl urea (DABCO® NE1060, DABCO® NE1070), N,N'-bis(3-dimethylaminopropyl)urea (DABCO® NE1060, DABCO® NE1070), bis(dimethylamino)-2-propanol, 6-dimethylamino-1-hexanol, N-(3-aminopropyl)imidazole, N-(2-hydroxypropyl)imidazole, and N-(2-hydroxyethyl)imidazole. The amount of tertiary amine will normally range from about 0.01 pphp to about 20 pphp and typically from about 0.05 pphp to about 10 pphp.

Exemplary blowing catalysts containing isocyanate reactive groups include 2-[N-(dimethylaminoethoxyethyl)-N-methylamino]ethanol (DABCO® NE200), dim ethylaminoethoxyethanol and N,N,N'-trimethyl-N'-3-aminopropyl-bis (aminoethyl)ether (DABCO® NE300). The amount of blowing catalyst will normally range from about 0.01 pphp to about 10 pphp and typically about 0.05 to about 5.0 pphp.

The catalyst may also comprise tertiary amines that are highly volatile and not isocyanate-reactive. Suitable volatile gelling catalysts may include, for example, diazabicyclooctane (triethylenediamine), supplied commercially as DABCO 33-LV® catalyst, tris(dimethylalminopropyl)amine (Polycat® 9), dim ethylaminocyclohexylamine (Polycat® 8) and bis(dimethylaminopropyl)-N-methylamine (Polycat® 77). Suitable volatile blowing catalysts include, for example, bis-dimethylaminoethyl ether, commercially supplied as DABCO® BL-11 catalyst by Air Products and Chemicals, Inc.; as well as pentamethyldiethylenetriamine (POLYCAT® 5, Air Products and Chemicals, Inc.) and related compositions; higher permethylated polyamines; 2-[N-(dimethylaminoethoxyethyl)-N-methylamino]ethanol and related structures; alkoxylated polyamines; imidazole-boron compositions; or amino propyl-bis(amino-ethyl)ether compositions. The amount of the foregoing catalyst will normally range from about 0.01 pphp to about 20 pphp and typically about 0.05 pphp to about 10.0 pphp.

The catalyst compositions may also include other components, for example transition metal catalysts such as organotin compounds, salts of tin, organobismuth and bismuth salts, for example when the desired polyurethane foam is a flexible slab stock. Additional examples of metal catalyst comprise dibutylin dilaureate, dimethyltin dilaureate, dimethyltin diacetate, dibutyltin diacetate, dimethyltin dilaurylmercaptide, dibutyltin dilaurylmercaptide, dimethyltin diisooctylmaleate, dibutyltin diisooctylmaleate, dim ethyltin bi(2-thylhexyl mercaptacetate), dibutyltin bi(2-thylhexyl mercaptacetate), stannous octate, other suitable organotin catalysts, or a combination thereof. Other metals can also be included, such as, for example, bismuth (Bi). Suitable bismuth carboxylate salts includes salts of pentanoic acid, neopentanoic acid, hexanoic acid, 2-ethylhexyl carboxylic acid, neohexanoic acid, octanoic acid, neooctanoic acid, isooctanic acid, heptanoic acid, neoheptanoic acid, isoheptanoic acid, nonanoic acid, neononanoic acid, isononanoic acid, decanoic acid, isodecanoic acid, neodecanoic acid, undecanoic acid, isounecanoic acid, neoundecanoic acid, dodecanoic acid, neododecanoic acid, isododecanoic acid, and other suitable carboxylic acids. Other salts of transition metals of mercury (Hg), lead (Pb), iron (Fe), zinc (Zn) with pentanoic acid, neopentanoic acid, hexanoic acid, 2-ethylhexyl carboxylic acid, octanoic acid, neooctanoic acid, neoheptanoic acid, neodecanoic acid, neoundecanoic acid, neododecanoic acid, and other suitable carboxylic acids may also be included. The amount of metal catalyst, if present, will normally range from about 0 pphp to about 10 pphp and typically about 0 pphp to about 5 pphp. Typically, the loading of non-fugitive tertiary amine catalyst(s) for making foam according to the invention will be in the range of 0.1 to 20 pphp, more typically 0.1 to 10 pphp, and most typically 0.1 to 5 pphp. However, any effective amount may be used. The term "pphp" means parts per hundred parts polyol.

Referring again to FIG. 1, in another embodiment, the process 100 includes contacting a tetraalkylguanidine 105 (step 104) with the aromatic carboxylic acid component 103 in the pre-mix 101, thereby forming a tetraalkylguanidine salt of the aromatic carboxylic acid 107 within the intermediate mix 129 (step 106). The contacting (step 104) of the tetraalkylguanidine 105 with the aromatic carboxylic acid component 103 in the pre-mix 101 is by any suitable procedure. In one embodiment, the tetraalkylguanidine 105 and the aromatic carboxylic acid component 103 in the pre-mix 101 are blended for a predetermined duration (for example, about 10 minutes), with a predetermined mixer (for example, a mechanical mixer 131), at a predetermined blade rotation speed (for example, about 5000 revolutions per minute), within a predetermined temperature range (for example, between about 21° C. and about 25° C.), or a combination thereof. The blending forms the intermediate mix 129 including the tetraalkylguanidine salt of the aromatic carboxylic acid 107 (step 106) that is capable of functioning as the catalyst composition 111 or a portion of the catalyst composition 111.

In one embodiment, the process 100 continues by mixing a tertiary amine catalyst component 113 into the catalyst composition 111 (step 108). The tertiary amine catalyst component 113 is mixed separately with the tetraalkylguanidine 105, is in the pre-mix 101 prior to the tetraalkylguanidine salt of aromatic carboxylic acid 107 being formed, is added to the pre-mix 101 after the tetraalkylguanidine salt of aromatic carboxylic acid 107 is formed, or a combination thereof. The mixing (step 108) is for a predetermined duration (for example, about 10 seconds), at a predetermined blade rotation speed (for example, about 6,000 revolutions per minute), or a combination thereof. Suitable tertiary amine catalysts can contain an isocyanate-reactive group or not. Isocyanate reactive groups comprise primary amine, secondary amine, hydroxyl group, amide or urea. Tertiary amine catalysts containing isocyanate reactive groups include both gelling and blowing catalysts. Exemplary gelling catalysts include N,N-bis(3-dimethylamino-propyl) N-isopropanolamine; N,N-dimethylaminoethyl-N'-methyl ethanolamine (DABCO® T, Air Products and Chemicals, Inc. of Allentown, Pa.); N,N,N'-trimethylaminopropyl ethanolamine (POLYCAT® 17, by Air Products and Chemicals, Inc.), N,N-dimethylethanolamine (DABCO® DMEA); N,N-dimethyl-N',N'-2-hydroxy(propyl)-1,3-propylenediamine; dimethylaminopropylamine (DMAPA); (N,N-dimethylaminoethoxy)ethanol, methyl-hydroxy-ethyl-piperazine, bis(N,N-dimethyl-3-aminopropyl)amine (POLYCAT® 15), N,N-dimethylaminopropyl urea (DABCO® NE1060, DABCO® NE1070), N,N'-bis(3-dimethylaminopropyl)urea (DABCO® NE1060, DABCO® NE1070), bis(dimethylamino)-2-propanol, 6-dimethylamino-1-hexanol, N-(3-aminopropyl)imidazole, N-(2-hydroxypropyl)imidazole, and N-(2-hydroxyethyl)imidazole. The amount of tertiary amine will normally range from about 0.01 pphp to about 20 pphp and typically from about 0.05 pphp to about 10 pphp.

Exemplary blowing catalysts containing isocyanate reactive groups include 2-[N-(dimethylaminoethoxyethyl)-N-methylamino]ethanol (DABCO® NE200), dimethylaminoethoxyethanol and N,N,N'-trimethyl-N'-3-aminopropyl-bis (aminoethyl)ether (DABCO® NE300). The amount of blowing catalyst will normally range from about 0.01 pphp to about 10 pphp and typically about 0.05 to about 5.0 pphp.

The catalyst may also comprise tertiary amines that are highly volatile and not isocyanate-reactive. Suitable volatile gelling catalysts may include, for example, diazabicyclooctane (triethylenediamine), supplied commercially as DABCO 33-LV® catalyst, tris(dimethylalminopropyl)amine (Polycat® 9), dimethylaminocyclohexylamine (Polycat® 8) and bis(dimethylaminopropyl)-N-methylamine (Polycat® 77). Suitable volatile blowing catalysts include, for example, bis-dimethylaminoethyl ether, commercially supplied as DABCO® BL-11 catalyst by Air Products and Chemicals, Inc.; as well as pentamethyldiethylenetriamine (POLYCAT® 5, Air Products and Chemicals, Inc.) and related compositions; higher permethylated polyamines; 2-[N-(dimethylaminoethoxyethyl)-N-methylamino]ethanol and related structures; alkoxylated polyamines; imidazole-boron compositions; or amino propyl-bis(amino-ethyl)ether compositions. The amount of the foregoing catalyst will normally range from about 0.01 pphp to about 20 pphp and typically about 0.05 pphp to about 10.0 pphp.

In other embodiments, the tertiary amine catalyst component 113 is not included and the catalyst composition 111 is used without a tertiary amine.

In one embodiment, the composition produced is the polyurethane composition 115. In this embodiment, the process 100 continues after the forming of the tetraalkylguanidine salt of aromatic carboxylic acid 107 (step 106) and/or after the catalyst mixing (step 108) with the polyurethane composition 115 being at least partially formed (step 110). The forming of the polyurethane composition 115 (step 110) includes combining an isocyanate component 117 with the pre-mix 101 and/or the intermediate mix 129. The combining is for a predetermined duration (for example, about 6 seconds), at a predetermined blade rotation speed (for example, about 6,000 revolutions per minute), or a combination thereof.

In one embodiment, the isocyanate component 117 is combined with the catalyst composition 111 at or about a stoichiometric ratio. In one embodiment, the stoichiometric ratio is based upon an NCO index. The NCO index is the number of equivalents of the isocyanate, divided by the total number of equivalents of active hydrogen, multiplied by 100 (for example, based upon an NCO index being [NCO/(OH+NH)]*100). The polyurethane composition 115 includes the NCO index being within a predetermined range. In one embodiment, the predetermined range is between about 80 and about 500. In a further embodiment, when the polyurethane composition 115 is used for producing flexible foams, the range is between about 80 and 120. In one embodiment, where the polyurethane composition 115 is used for producing a spray foam application, the range is between about 100 and about 500. In one embodiment, the polyurethane composition 115 is used with a trimerization catalyst to produce polyisocyanurate foams use in foam laminates and includes a range suitable for the use.

The isocyanate component 117 includes any suitable organic isocyanate compound. Suitable organic isocyanate compounds include, but are not limited to, hexamethylene diisocyanate (HDI), phenylene diisocyanate (PDI), toluene diisocyanate (TDI), 4,4'-diphenylmethane diisocyanate (MDI), isophoronedi-isocyanate (IPDI), or combinations thereof. In one embodiment, the isocyanate component 117 includes 2,4-TDI, 2,6-TDI, or a combination thereof. In one embodiment, the isocyanate component 117 includes, by weight, about 80% 2,4-TDI and about 20% or a remainder 2,6-TDI. In one embodiment, the isocyanate component 117 includes crude MDI, such as, a mixture of about 60% 4,4'-MDI and/or a stoichiometric amount along with other isomeric and analogous higher polyisocyanates. Other suitable isocyanates are shown and described in U.S. Pat. No. 4,394,491, which is hereby incorporated by reference in its entirety.

In one embodiment, the pre-mix 101, intermediate mix 129, and/or the polyurethane composition 115 include(s), by weight, at least about 20% being the polyol component 109, between about 0.5% and about 10% being the surfactant component 123, between about 2% and about 4.5% being the blowing agent component 125, between about 0.5% and about 2% being the crosslinking component 127, between about 0.25% and about 10% being the catalyst composition 111, with the amount of the isocyanate component 117 being based upon the NCO index being between about 70 and about 115. In a further embodiment, the polyol component 109 includes polymer polyol, natural oil polyol, and/or other suitable copolymers. In one embodiment, the polyurethane composition 115 has an average molecular weight between about 4,000 and about 5,000 and/or a hydroxyl number between about 28 and about 35.

In one embodiment, the pre-mix 101, the intermediate mix 129, and/or the polyurethane composition 115 include(s) about 100 pphp being the polyol component 109 (for example, about 50 pphp being a polyester polyol and/or about 50 pphp being a polyether polyol), about 0.25 pphp being the surfactant component 123, about 3.06 pphp being water, and the isocyanate component 117 having an NCO index of about 120. The pre-mix 101, the intermediate mix 129, and/or the polyurethane composition 115 also include(s) the catalyst composition 111. In a further embodiment, the pre-mix 101, the intermediate mix 129, and/or the polyurethane composition 115 include(s) about 21.5 pphp being the flame retardant (for example, tris-(2-chloropropyl) phosphate).

In one embodiment, the pre-mix 101, the intermediate mix 129, and/or the polyurethane composition 115 include(s) about 99.40 pphp being the polyol component 109 (for example, about 90.40 pphp being a polyether polyol(triol) with OH of about 28 and about 9.00 pphp being 1,4-butane diol), about 0.1 pphp being the surfactant component 123 (for example, silicon surfactant), about 0.50 pphp being a molecular sieve powder (for example, 3A), about 100 pphp being the isocyanate component 117 (for example, an elastomeric type of MDI with an NCO index number of about 27.5), or combinations thereof.

A base polyol in the polyol component 109 reacts with the isocyanate 117 to produce the polyurethane composition 115. Suitable base polyols are shown and described in WO 03/016373 A1, WO 01/58976 A1, WO 04/060956 A1, WO 03/016372 A1, and WO 03/055930 A1, each of which are hereby incorporated by reference in their entirety. Suitable base polyols include, but are not limited to, polyether polyols. In one embodiment, the polyether polyols are poly(alkylene oxide) polymers, such as, poly(ethylene oxide), poly(propylene oxide), and/or copolymers with terminal hydroxyl groups derived from polyhydric compounds (for example, diols and triols). In one embodiment, the diols and triols utilized are ethylene glycol, propylene glycol, 1,3-butanediol, 1,4-butanediol, 1,6-hexanediol, neopentyl glycol, diethylene glycol, dipropylene glycol, pentaerythritol, glycerol, diglycerol, trimethylol propane, other suitable low molecular weight polyols, or combinations thereof. In one embodiment, the base polyol is or includes polyhydroxy-terminated acetal resin, hydroxy-terminated amine, hydroxyl-terminated polyamine, or a combination thereof. In one embodiment, the base polyol is or includes polyalkylene carbonate-based polyols, phosphate-based polyols, or combinations thereof.

In one embodiment, the base polyol is a single high molecular weight polyether polyol. In another embodiment, the base polyol is a mixture of high molecular weight polyether polyols, each having a different molecular weight or different chemical composition. In this embodiment, the base polyol includes di-functional and tri-functional materials, such as, but not limited to, polyethylene glycol, polypropylene glycol, glycerol-based polyether triols, trimethylolpropane-based polyether triols, other similar ester-free compounds or mixtures, or combinations thereof. In one embodiment, the base polyol includes an ester-free polyol component at a concentration, by weight, of at least about 50%, the ester-free polyol component including one or more polyether polyols.

Additionally or alternatively, in one embodiment, the base polyol is or includes copolymer polyols. The copolymer polyols form, by weight, up to about 80% of the total polyol content (the total polyol content being based upon the amount of base polyol, natural polyols, and any other polyols in the polyurethane composition 115). The copolymer polyols improve polyurethane foam formed by the polyurethane composition 115 by increasing resistance to deformation of the polyurethane foam, thereby increasing load-bearing properties of a polyurethane foam formed by the polyurethane composition 115. In one embodiment, the copolymer polyol is or includes a graft polyol, a polyurea modified polyol, or a combination thereof.

The graft polyol is any suitable graft polyol. In one embodiment, the graft polyol is prepared by copolymerizing vinyl monomers (for example, styrene and acrylonitrile) with a suitable starting polyol. In one embodiment, the starting polyol is or includes glycerol-initiated triol, end-capped with ethylene oxide (for example, at about 80% to about 85% primary hydroxyl groups). In this embodiment, the graft polyol includes copolymer grafted to the starting polyol, homopolymers of the vinyl monomers, and the starting polyol (unaltered). In one embodiment, the graft polymer includes the styrene or acrylonitrile at a concentration, by weight, between about 5% and about 45%.

In one embodiment, the polyurea modified polyol is formed by the reaction of a diamine and a diisocyanate in the presence of the starting polyol. In this embodiment, the polyurea modified polyol includes polyurea dispersion. In one embodiment, the polyurea modified polyol is or includes polyisocyanate poly addition (PIPA) polyols, for example, formed in situ from a reaction of the isocyanate 117 and an alkanolamine in the starting polyol.

In one embodiment, the base polyol is or includes a natural oil polyol. Generally, the natural oil polyols are less expensive and from renewable resources, thereby providing environmental benefits. The natural oil polyols include triglycerides of saturated and/or unsaturated acids having a carbon chain length between 12 and 24. The saturated acids are lauric acid, myristic acid, palmitic acid, steric acid, arachidic acid, lignoceric acid, or a combination thereof. The unsaturated acids are mono-unsaturated (for example, palmitoleic acid, oleic acid, or a combination thereof) and/or poly-unsaturated (for example, linoleic acid, linolenic acid, arachidonic acid, or a combination thereof).

In one embodiment, the natural oil polyol used as or in the base polyol is castor oil. The castor oil is a natural triglyceride of ricinoleic acid having a low hydroxyl content.

In one embodiment, a natural oil or fat is modified to form the natural oil polyol. In this embodiment, an epoxidized natural oil is reacted with a ring opening acid catalyst and a ring opener. The epoxidized natural oil is a plant-based oil, such as epoxidized vegetable oil and/or epoxidized animal fat. Suitable epoxidized natural oils that are plant-based oils include, but are not limited to, soybean oil, corn oil, sunflower oil, olive oil, canola oil, sesame oil, palm oil, rapeseed oil, tung oil, cottonseed oil, safflower oil, peanut oil, linseed oil, or a combination thereof. Suitable epoxidized natural oils that are epoxidized animal fat are fish fat, tallow, lard, or a combination thereof. Other suitable epoxidized natural oils are shown and described in WO 06/116456 A1, which is hereby incorporated by reference in its entirety.

In one embodiment, the natural oil or the fat is modified by increasing hydroxy content through chemical reaction at unsaturated sites and/or at ester functional groups. For example, in one embodiment, the unsaturated sites are hydroxylated via epoxidation/ring opening and/or hydroformylation/hydrogenation. In one embodiment, the ring opening of the epoxidized natural oil is with alcohol, water, and other compounds having one or more nucleophilic groups. In a further embodiment, the epoxidized natural oil is also oligomerized. In one embodiment, the hydroformylation/hydrogenation of the epoxidized natural oil is in a reactor (not shown) filled with a hydrogen/carbon monoxide mixture in the presence of a suitable catalyst (for example, cobalt, rhodium, or combinations thereof) to form an aldehyde that is hydrogenated in the presence of a cobalt catalyst or a nickel catalyst to form a polyol.

In one embodiment, ester functional groups in suitable reactants are modified by trans-esterification to introduce hydroxy groups. In this embodiment, a suitable polyhydroxy containing substance and trans-esterification catalyst (for example, an alkali metal or alkali earth metal base or salt) produce the polyol of the natural oil or fat. The trans-esterification includes any suitable natural oil or partially hydrogenated oil. Suitable natural oils include, but are not limited to, soybean, corn, cottonseed, peanut, castor, sunflower, canola, rapeseed, safflower, fish, seal, palm, tung, olive oil, or combinations thereof. Suitable multifunctional hydroxyl compounds include, but are not limited to, lactose, maltose, raffinose, sucrose, sorbitol, xylitol, erythritol, mannitol, or combinations thereof.

In one embodiment, the polyol component 109 includes polyols for making rigid polyisocyanurate foam. Such polyols include, but are not limited to, polyalkylene ether and polyester polyols. In one embodiment, the polyalkylene ether includes a poly(alkyleneoxide) polymer, such as, poly (ethyleneoxide) and poly(propyleneoxide) polymers and copolymers with terminal hydroxyl groups derived from polyhydric compounds including diols and triols, for example, among others, ethylene glycol, propylene glycol, 1,3-butane diol, 1,4-butane diol, 1,6-hexane diol, neopentyl glycol, diethylene glycol, dipropylene glycol, pentaerythritol, glycerol, diglycerol, trimethylol propane, cyclohexane diol, sugars such as sucrose and like low molecular weight polyols, or combinations thereof. In another embodiment, the polyol component 109 includes amine polyether polyols that can be prepared when an amine, such as ethylenediamine, diethylenetriamine, tolylenediamine, diphenylmethanediamine, triethanolamine, or the like, is reacted with ethylene oxide or propylene oxide. In one embodiment directed to spray foam formulation, the polyol component 109 includes polyether polyols, thereby increasing reactivity of the polyurethane composition 115. In one embodiment, the polyether polyols are prepared by condensation of phenol with formaldehyde in the presence of hydroxyl-containing amines such as diethanolamine, ethanolamine, and the like.

In one embodiment, the polyol component 109 includes a single high molecular weight polyether polyol. Additionally or alternatively, in one embodiment, mixtures of high molecular weight polyether polyols, such as mixtures of different multifunctional materials and/or different molecular weight or different chemical composition, are included in the polyol component 109.

In one embodiment, the polyol component 109 includes a polyester polyol produced when a dicarboxylic acid is reacted with an excess of a diol, for example, adipic acid, phathalic acid, phthalic anhydride with ethylene glycol, or butanediol, or when a lactone is reacted with an excess of a diol, such as, caprolactone with propylene glycol.

In one embodiment, the polyurethane composition 115 includes increased foam kinetics in comparison to known polyurethane compositions. Such properties include, but are not limited to, a decreased use level of the catalyst composition 111 (for example, from about 2.8 pphp to about 2.0 pphp), an earlier start time (for example, at about 10 seconds instead of about 11 seconds), an earlier rise time (for example, at about 24 seconds instead of about 29 seconds), an increased maximum velocity (for example, at about 23 mm/s instead of about 22 mm/s), a decreased maximum height (for example, at about 167 mm instead of about 180 mm), a decreased final height (for example, at about 165 mm instead of about 178 mm), an increased shrinkage (for example, about 1.4 instead of 1.1), or a combination thereof. One or more of the properties of the polyurethane composition 115 is indicative of a front end delay on curing.

In one embodiment, the polyurethane composition 115 includes foam stability when exposed to adverse environmental conditions such as hot and humid environments, particularly in comparison to known polyurethane products. For example, in one embodiment, the polyurethane composition 115 has an increased resistance to degradation under such conditions in comparison to known polyurethane compositions.

In one embodiment, the process 100 continues with the polyurethane composition 115 being poured (step 112), for example, by pouring it into a pre-heated mold 119. In one embodiment, the pre-heated mold 119 is at a predetermined temperature (for example, about 70° C., between about 61° C. and about 65° C., or any combination or sub-combination thereof), the polyurethane composition 115 remains in the pre-heated mold 119 for a predetermined duration (for example, at least about 4 minutes), or a combination thereof. Additionally or alternatively, the process 100 continues with the polyurethane composition 115 being cured (step 114).

Among other things, the curing (step 114) of the polyurethane composition 115 is dependent upon the components of the pre-mix 101 and/or the intermediate mix 129, the catalyst composition 111, and the tertiary amine catalyst component 113 (if included). For example, the catalyst composition 111 retards the curing (step 114) and/or decreases temperature dependence by including the tetraalkylguanidine salt of the aromatic carboxylic acid 107. Specifically, the tetraalkylguanidine salt of the aromatic carboxylic acid 107 increases catalysis of a gelling reaction occurring between the isocyanate 117 and a polyol in the pre-mix 101 and/or the intermediate mix 129 when forming a polymer, such as the polyurethane composition 115.

In one embodiment, the catalyst composition 111 includes the tetraalkylguanidine salt of aromatic carboxylic acid 107 and the tertiary amine catalyst component 113. In another embodiment, the catalyst composition 111 includes the tetraalkylguanidine 105 and the tertiary amine catalyst component 113. The tertiary amine catalyst component 113 further retards the curing (step 114) by delaying polymerization, for example, until the pre-heated mold 119 is filled with the polyurethane composition 115. The tertiary amine catalyst component 113 is or includes a single tertiary amine catalyst or a combination of tertiary amine catalysts. The tertiary amine catalyst component 113 is or includes a fugitive tertiary amine catalyst or a non-fugitive tertiary amine catalyst. In one embodiment, the tertiary amine catalyst component 113 is a non-fugitive tertiary amine catalyst at a predetermined amount of pphp, such as, between about 0.1 pphp and about 20 pphp, between about 0.1 pphp and about 10 pphp, between about 0.1 pphp and about 5 pphp, or any suitable combination or sub-combination thereof.

The tertiary amine catalyst component 113 includes or does not include an isocyanate reactive group. In one embodiment, the catalyst composition 111 including or not including the tertiary amine catalyst component 113 permits the polyurethane composition 115 to flow into a complex mold having a complex geometry (for example, multiple vents, such as five vents, each about 1.5 mm in diameter), prior to completion of the curing (step 114). In one embodiment, the complex mold includes a solvent-based release agent. Adjustments of the rate of the curing (step 114) permit decreased intensity of energy to be used, more efficient filling of the pre-heated mold 119, and reduced or eliminated sacrifice of mold productivity.

In one embodiment, the tertiary amine catalyst component 113 augments the tetraalkylguanidine salt of aromatic carboxylic acid 107 by including an isocyanate reactive group and further retards curing (step 114) and further decreases temperature dependence. For example, in one embodiment, the tertiary amine catalyst component 113 is or includes N,N-bis(3-dimethylaminopropyl)-N-isopropanolamine, N,N-dimethylaminoethyl-N'-methyl ethanolamine, N,N,N'-trimethylaminopropyl ethanolamine, N,N-dimethylethanolamine, N,N-dimethyl-N',N'-2-hydroxy(propyl)-1,3-propylenediamine, dimethylaminopropylamine, (N,N-dimethylaminoethoxy)ethanol, methyl-hydroxy-ethyl-piperazine, bis(N,N-dimethyl-3-aminopropyl)amine, N,N-dimethylaminopropyl urea, N,N'-bis(3-dimethylaminopropyl) urea, bis(dimethylamino)-2-propanol, N-(3-aminopropyl)imidazole), N-(2-hydroxypropyl)imidazole, and N-(2-hydroxyethyl)imidazole, or combinations thereof. Additionally or alternatively, in one embodiment, the tertiary amine catalyst component 113 is or includes a blowing catalyst component 125. For example, in one embodiment, the tertiary amine catalyst component 113 is or includes 2-[N-(dimethylaminoethoxyethyl)-N-methylamino]ethanol, N,N-dimethylaminoethyl-N'-methyl-N'-ethanol, dimethylaminoethoxyethanol, N,N,N'-trimethyl-N'-3-aminopropyl-bis(aminoethyl) ether, or combinations thereof. The amount of such tertiary amine catalyst component typically ranges from about 0.01 pphp to about 20 pphp and typically from about 0.05 pphp to about 10 pphp.

In one embodiment, the tertiary amine catalyst component 113 is highly volatile and is not isocyanate-reactive. For example, in one embodiment, the tertiary amine catalyst component 113 is a volatile gelling catalyst and is or includes diazobicyclooctane (triethylenediamine), 1,8-diazabicycloundec-7-ene, tris(dimethylaminopropyl)amine, dimethylaminocyclohexylamine, bis(dimethylaminopropyl)-N-methylamine, or combinations thereof. Additionally or alternatively, in one embodiment, the tertiary amine catalyst component 113 is or includes a volatile blowing catalyst and is or includes bis-dimethylaminoethyl ether, pentamethyldiethylenetriamine, hexamethyltriethylenetetramine, heptamethyltetraethylenepentamine and related compositions, higher permethylated polyamines, 2[N-(dimethylaminoethoxyethyl)-N-methylamino]ethanol and related structures, alkoxylated polyamines, imidazole-boron compositions, amino propyl-bis(amino-ethyl)ether compositions, or combinations thereof.

In one embodiment, the tertiary amine catalyst component 113 is used in conjunction with a transition metal catalyst. For example, in one embodiment, the tertiary amine catalyst component 113 is used with an organotin compound, tin(II) carboxylate salts, bismuth(III) carboxylate salts, or combinations thereof. In the embodiments without the tertiary amine catalyst component 113, the catalyst composition 111 having the tetraalkylguanidine salt of aromatic carboxylic acid 107 is used with or without such transition metal catalysts. In an embodiment where the catalyst composition 111 is used without the tertiary amine catalyst component 113 or transition metal catalyst, the tetraalkylguanidine salt of aromatic carboxylic acid 107 is at a predetermined amount, for example, between about 0.1 and about 20 parts per million (ppm), between about 0.1 and about 10 ppm, between about 0.1 and about 5.0 ppm, or any suitable combination or sub-combination thereof.

In one embodiment, the catalyst composition 111 includes a predetermined amount of tertiary amine catalyst component 113 and the tetraalkylguanidine salt of aromatic carboxylic acid 107. For example, in one embodiment, the catalyst composition 111 includes N,N'-bis(3-dimethylaminopropyl) urea (for example, about 0.40 pphp) and N,N,N'-trimethyl-N'-3-aminopropyl-bis(aminoethyl)ether (for example, 0.17 pphp) being in the tertiary amine catalyst component 113 and the tetraalkylguanidine salt of aromatic carboxylic acid 107 (for example, about 0.52 pphp or about 0.90 pphp). In another embodiment, the catalyst composition 111 includes tris-(n,N-dimethylaminopropyl)amine and bis-(N,N-dimethylaminopropyl)-N'-methylamine being in the tertiary amine catalyst component 113 (for example, at about 88% by weight). In a further embodiment, the catalyst composition 111 includes the tetraalkylguanidine salt of aromatic carboxylic acid 107 (for example, at about 12% by weight). In a further embodiment, the tetraalkylguanidine salt of aromatic carboxylic acid 107 includes one more of phthalic acid per two moles of the tetraalkylguanidine 105. In another embodiment, the catalyst composition 111 includes 1,8-diazabicycloundec-7-ene (for example, at about 0.1456 pphp), the tetraalkylguanidine salt of aromatic carboxylic acid 107 (for example, at about 0.12 pphp), an acid blocking agent with aromatic character (for example, at about 0.1344 pphp), an amine to acid ratio of about 5.6, or a combination thereof.

In one embodiment, the catalyst composition 111 is configured to extend pot life. For example, in one embodiment, the catalyst composition 111 includes the tetraalkylguanidine salt of aromatic carboxylic acid 107 and a suitable acid having low aromatic character. Suitable acids include, but are not limited to, benzoic acid (having about 59% aromatic character), phthalic acid (having about 43% aromatic character), phenyl-propionic acid (having about 48% aromatic character, an acid blocking agent (for example, having about 19% aromatic character), or combinations thereof, and the molar ratio of tetraalkylguandine to carboxylic acid groups in the aromatic carboxylic acid typically ranges from about 0.7 to about 1.3 Without wishing to be bound by any theory or explanation, it is believed that the extended pot life attributable to the inclusion of the acid having the low aromatic character extends pot life for a predetermined duration (for example, from about 38 seconds to about 65 seconds, about 80 seconds, about 121 seconds, or longer). Pot life extension is determined automatically using instrumentation that measures the changes in viscosity over time. Additionally or alternatively, in one embodiment, the acid having the low aromatic character extends fiber time (for example, from about 74 seconds to about 107 seconds, about 131 seconds, about 170 seconds, or longer) and/or non-fiber time (for example, from about 94 seconds to about 113 seconds, about 163 seconds, about 212 seconds, or longer).

Figure 2:
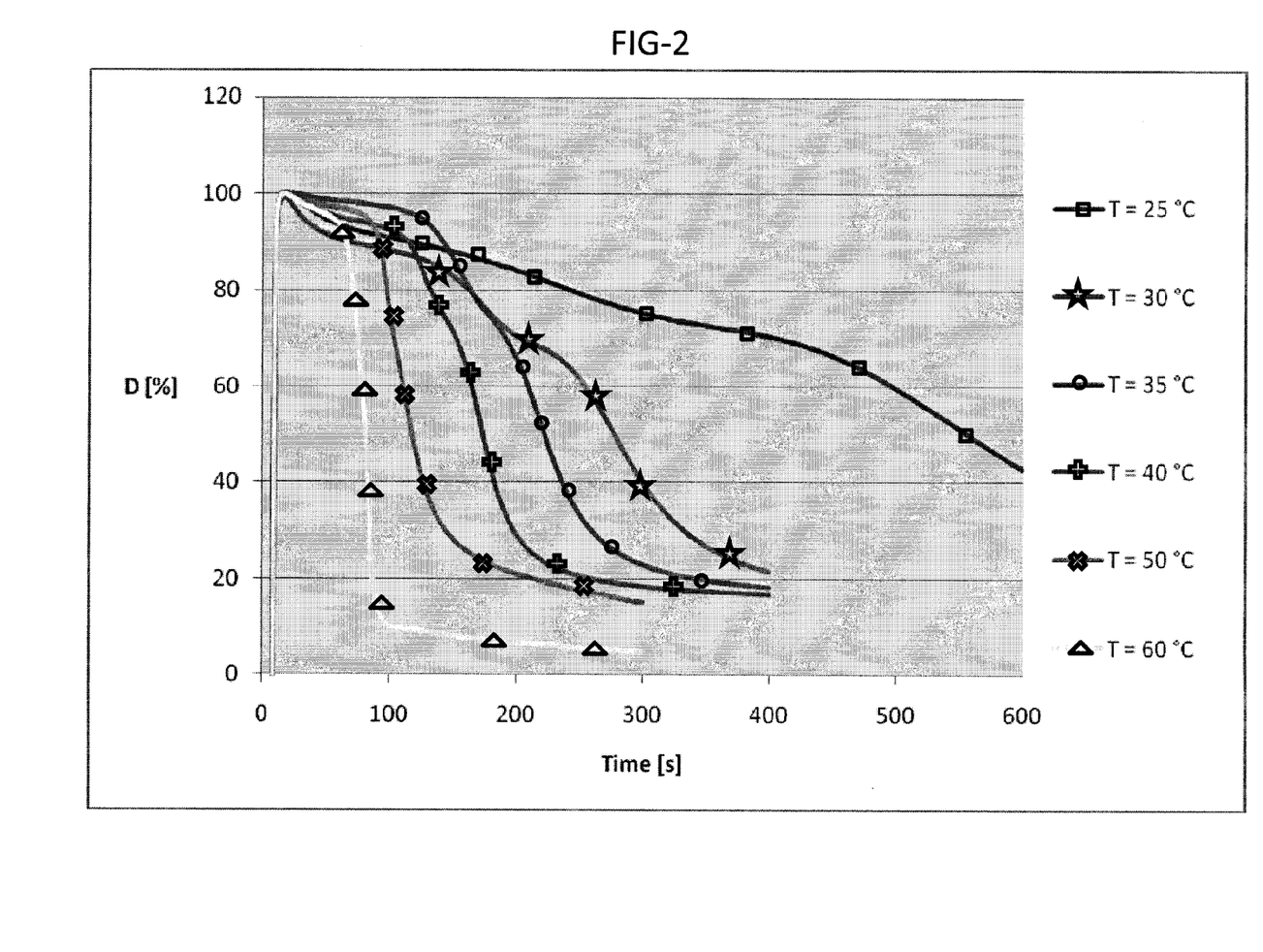
FIG. 2 is a cure profile of a polyurethane composition.
Figure 3:
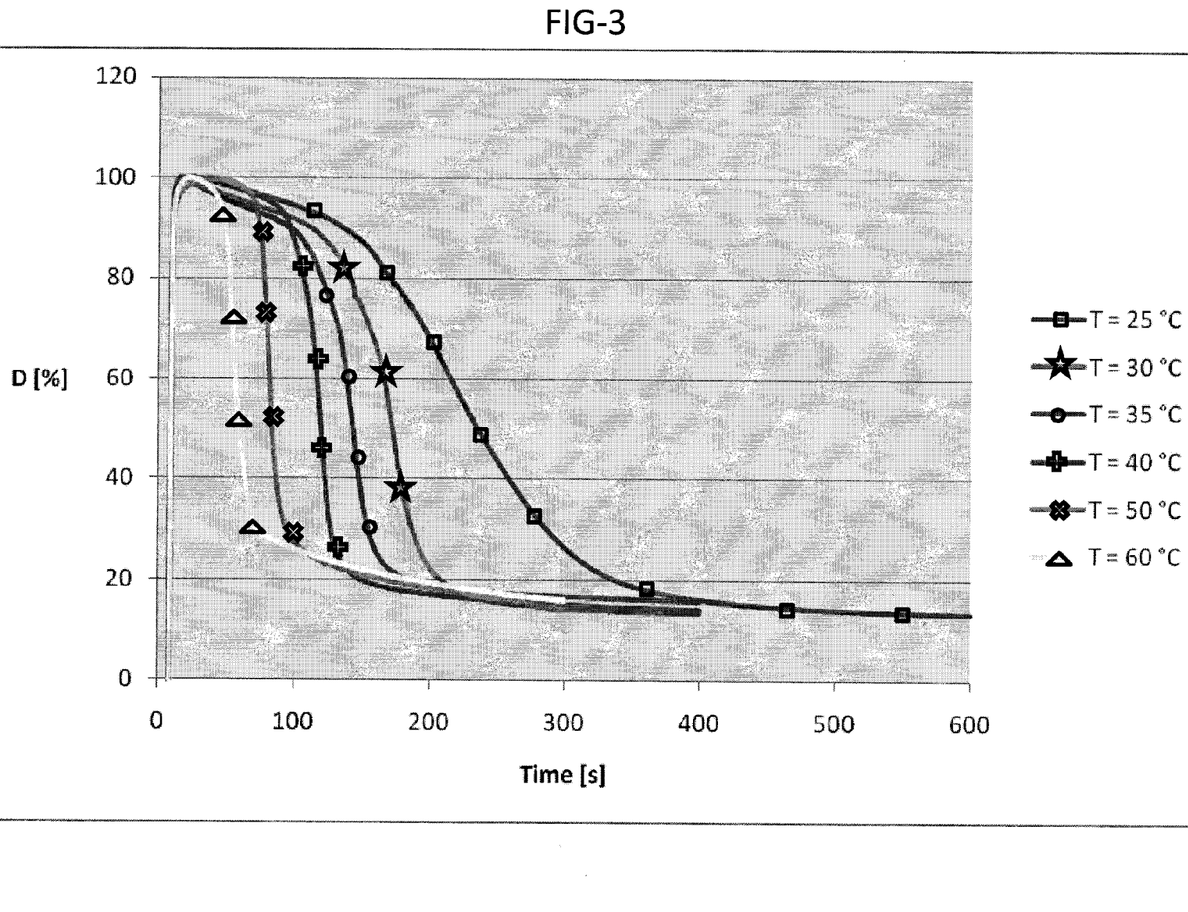
FIG. 3 is a cure profile of a polyurethane composition containing a tertiary amine catalyst.
Figure 4:
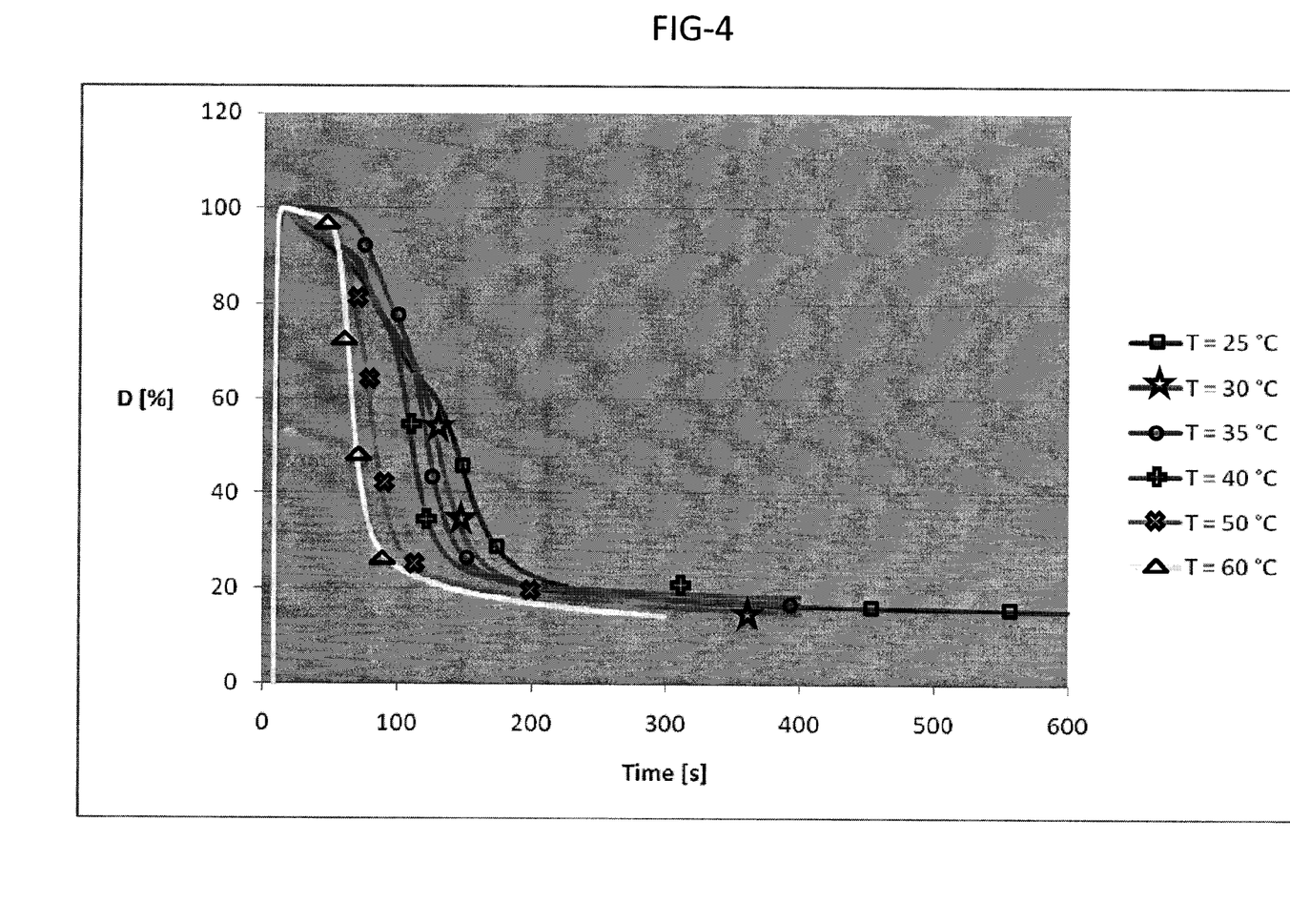
FIG. 4 is a cure profile of an exemplary polyurethane composition containing a tertiary amine catalyst and a tetraalkylguanidine salt of aromatic carboxylic acid.

In one embodiment, the catalyst composition 111 is adjusted to achieve a predetermined cure profile. For example, referring to FIGS. 2-4, in one embodiment, the curing (step 114) of the polyurethane composition 115 to form the product 121 is temperature and time dependent. FIG. 2 shows a known cure profile for a known polyurethane product without the tetraalkylguanidine salt of aromatic carboxylic acid 107 or the tertiary amine catalyst component 113. The lower temperature curing is distinguishable (for example, maintaining a 60% dielectric constant at up to about 500 seconds at a temperature of about 25° C. in comparison to 80 seconds at a temperature of about 60° C.) and shows the temperature dependence. FIG. 3 shows a cure profile for a polyurethane product without the tetraalkylguanidine salt of aromatic carboxylic acid 107 but with the tertiary amine catalyst component 113. Overall, the curing is less temperature dependent, including for the lower temperature curing (for example, maintaining a 60% dielectric constant at up to about 210 seconds at a temperature of about 25° C. in comparison to 60 seconds at a temperature of about 60° C.). FIG. 4 shows the cure profile of the polyurethane composition 115 forming the product 121 described herein. In FIG. 4, the curing (step 114) is less temperature dependant (for example, maintaining a 60% dielectric constant at up to about 150 seconds at a temperature of about 25° C. in comparison to 60 seconds at a temperature of about 60° C.).

The process 100 continues with the polyurethane composition 115 being removed from the pre-heated mold 119 as a product 121 (step 116), such as, a flexible foam (for example, as in automobile interiors), an adhesive, a sealant, an elastomer, a rigid foam (for example, as used in commercial and residential areas with foam spraying techniques), and/or a microcellular foam (for example, as in shoe soles or foamed sealants). In one embodiment, the product 121 is removed from the pre-heated mold 119 after a predetermined duration (for example, about 4 minutes).

Using the process 100 to form the product 121 permits the product 121 to have properties not previously available. In one embodiment, the properties of the product 121 formed from the polyurethane composition 115 are impacted by including the blowing agent component 125 in the polyurethane composition 115. The blowing agent component 125 forms voids in a polyurethane matrix of the product 121 by having low boiling points and being vaporized during the exothermic polymerization reaction. In one embodiment, the blowing agent component 125 is inert and does not decompose or react during the polymerization reaction. The blowing agent component 125 includes any suitable blowing agent. Suitable blowing agents include, but are not limited to, carbon dioxide, chlorofluorocarbons, hydrogenated fluorocarbons, hydrogenated chlorofluorocarbons, fluoroolefins, chlorofluoroolefins, hydrofluoroolefins, hydrochlorofluoro olefins, acetone, low-boiling hydrocarbons (for example, cyclopentane, isopentane, n-pentane, or combinations thereof), or combinations thereof. Other suitable blowing agents include, but are not limited to, compounds that react with isocyanate compounds to produce a gas (for example, water). In one embodiment, the pre-mix 101, the intermediate mix 129, and/or the polyurethane composition 115 include the blowing agent at a suitable amount. Suitable amounts include, but are not limited to, about 0 (water blown) to about 80 pphp, about 0 (water blown) to about 60 pphp (for example, with a very low density foam), about 1.0 pphp to about 10 pphp, about 2.0 pphp to about 5 pphp, or any suitable combination or sub-combination thereof. In embodiments with that are water blown, the isocyanate component 117 reacts, thereby forming carbon dioxide.

In one embodiment, the product 121 includes increased dimensional stability in comparison to known polyurethane products. Dimensional stability is determined by a standard ASTM D2126 method. In one embodiment, the product 121 includes increased thermal insulation in comparison to known polyurethane products. Thermal insulation properties are determined by measuring k-factor using standard ASTM C177 method.

In one embodiment, the product 121 includes low odor in comparison to known polyurethane products. The low odor is achieved by having a lower vapor pressure. For example, in one embodiment, the pre-mix 101, the intermediate mix 129, the polyurethane composition 115, and/or the product 121 show no amine or acidic emissions when tested according to VDA 278 protocol, commonly used for analyzing volatile organic compounds (VOCs), such as, in car interiors. Such low-VOC or no-VOC properties reduce or eliminate hazards for operators (such as spray operators), reduce or eliminate formation of airborne amines, and/or generally benefit the environment. VDA 278 protocol is a thermal desorption test method for standard polyurethane foam emissions generally known in the automotive industry. The protocol permits evaluation of polyurethane foam under aggressive conditions by measuring gaseous emissions that typically contribute to the contamination of the interior air quality of a car. This measurement is generally done for about 30 minutes at about 90° C. and subsequently for 60 minutes at about 120° C. Specifically, the protocol involves putting a sample into a thermal desorption tube that is continuously flushed with an inert gas for 30 minutes at about 90° C. The volatile emissions released from the sample are collected in a cryogenic trap at about −150° C. At the end of this period, trapped residue is heated to about 280° C. and injected into a gas chromatograph/mass spectrometer analytical system. Next, VOCs are measured by measuring the condensable emissions that are responsible for fogging in cars. The same sample is heated up to 120° C. and gas is passed through the sample for 60 minutes, while the volatiles are condensed in a cryogenic trap at about 150° C. The condensates are then heated up to about 280° C. and analyzed by gas chromatograph/mass spectrometer analytical system.

In one embodiment, the product 121 includes increased consistency of physical properties in comparison to known polyurethane products. For example, in one embodiment, the physical properties of the product 121 have greater consistency throughout the product 121, the physical properties are more reproducible, and/or the physical properties include increased mechanical strength. The mechanical strength is illustrated by Force-to-Crush (FTC) measurements illustrating dimensional stability as measured by using force detection device that is equipped with a 2.2 kg capacity pressure transducer mounted between the 323 $cm^2$ circular plate cross head and the drive shaft. The actual force is shown on a digital display. FTC measurements were conducted 45 seconds after demold. The pad was removed from the mold, weighed and placed in the FTC apparatus. This device mimics the ASTM D-3574, Indentation Force Deflection Test and provides a numerical value of freshly demolded foam's initial hardness or softness. The pad was compressed to 50 percent of its original thickness at a cross-head velocity of 275 mm per minute with the force necessary to achieve the highest compression cycle recorded in Newtons. Ten compression cycles were completed. A cycle takes approximately 30 seconds to complete.

For example, in one embodiment, the FTC measurements were based upon a predetermined duration of crushing (for example, about 1 minute), a predetermined amount of iterations per part (for example, about three times each part), with a predetermined amount of rotation (for example, 90 degree rotation), at predetermined conditions (for example, between about 21° C. and about 25° C. or between about 48% and about 52%), with a predetermined capacity pressure (for example, about 2.2 kg), and to a predetermined compression (for example, about 50% of an original thickness).

In one embodiment, the predetermined compression of the product 121 is greater than that of a similar product formed without the catalyst composition 111 (for example, 6.5% in comparison to about 5.2%). Product compression is determined by ASTM D3574 method and tests D & K. In a further embodiment, the predetermined compression of the product 121 is greater in the presence of a greater concentration of the tetraalkylguanidine salt of aromatic carboxylic acid 105 in the catalyst composition 111 (for example, 16% in comparison to about 6.5%).

In one embodiment, the product 121 has improved humid aged physical properties in comparison to a similar product formed without the catalyst composition 111 when measured in accordance with HALLS (70% preflex) aging; VW test method ISO-3386-1; VW HA-tensile DIN 53571 method and VWASTM D-3574 Test D @ 50% constant deflection compression set. For example, in one embodiment, humid aged load loss of the product 121 is decreased (for example, to about −2.8% from −20%) and/or is further increased in the presence of a greater concentration of the tetraalkylguanidine salt of aromatic carboxylic acid 107 (for example, to about 0.0%). Additionally or alternatively, in one embodiment, humid aged tensile strength of the product 121 is increased (for example, to 44 kPa from 38 kPa) and/or is further increased in the presence of a greater concentration of the tetraalkylguanidine salt of aromatic carboxylic acid 107 (for example, to about 61 kPa). Additionally or alternatively, in one embodiment, humid aged elongation of the product 121 is increased (for example, to 61% from 59%) and/or is further increased in the presence of a greater concentration of the tetraalkylguanidine salt of aromatic carboxylic acid 107 (for example, to about 67%). Additionally or alternatively, in one embodiment, humid aged compression of the product 121 is increased (for example, to 16% from 11%). in the presence of a greater concentration of the tetraalkylguanidine salt of aromatic carboxylic acid 105.

Certain embodiments of the invention are illustrated by the following Examples. These Examples do not limit the scope of the appended claims.

Example 1

Comparison of Flexible Polyurethane Polymers Foam Made with TMG Salts of Aromatic Carboxylic Acids and Standard Amine Catalysts Foam pads were prepared by adding a tertiary amine catalyst to about 302 g of a premix (prepared as in Table 2) in a 32 oz (951 ml) paper cup. The formulation was mixed for about 10 seconds at about 6,000 RPM using an overhead stirrer fitted with a 2-inch (5.1 cm) diameter stirring paddle.

The toluene diisocyanate was then added, and the formulation was mixed well for about another 6 seconds at about 6,000 RPM using the same stirrer, after which it was poured into a pre-heated mold at 70° C. and demolded after 4 minutes. The foam pads were removed from the mold, hand crushed, weighed and machine crushed at 75% pad thickness by passing the foam pads through two steel rolling cylinders separated at at distance equivalent to 25% of foam pad thickness. Foam pads were stored under constant temperature and humidity conditions for 48 hours before being cut and tested.

TABLE 1

Premix components

| Component | #1 PPHP |
| --- | --- |
| SPECFLEX ® NC 630[1] | 55 |
| SPECFLEX ® NC 700[2] | 45 |
| Water | 3.0 |
| DABCO ® DC6070[3] | 0.60 |
| Catalyst | Varied |
| Diethanolamine (crosslinker) | 0.70 |
| Toluene diisocyanate | To provide NCO index = 100 |

[1]High functionality capped polyether polyol of high molecular weight, functionality, and primary hydroxyl content with a base polyol molecular weight of about 5500, available from Dow Chemical Company, Midland, MI.
[2]Grafted polyether polyol containing copolymerized styrene and acrylonitrile, base polyol molecular weight about 4800, available from Dow Chemical Company, Midland, MI.
[3]Silicone surfactant is available from Air Products and Chemicals, Inc.
[4]The amine catalyst is available from Air Products and Chemicals, Inc.

Catalyst A in Table 2 is an aromatic carboxylate salt of TMG that was prepared by dissolving 20.8 g of phthalic acid in 50.3 g of PEG-200 and followed by reaction of this mixture with 28.9 g of TMG. This product was used in combination with standard amine catalysts Dabco® NE1070 and Dabco® NE300. Table 2 shows that when reducing the use level of control gelling catalyst Dabco® NE1070 and replacing with the TMG/phthalic acid catalyst no appreciable change occurs in the speed of foam curing (as shown by the similar string gel times) indicating that the productivity of the process is not compromised by the use of the acid-blocked TMG catalyst. This was very surprising because acid blocked catalysts are normally able to promote the polyurethane reactions at a much slower rate than non-acid blocked catalysts.

TABLE 2

Catalyst combinations.

| Foam | Daboc ® NE1070 | Dabco ® NE300 | Catalyst 1 | SGT (sec) |
| --- | --- | --- | --- | --- |
| A (control) | 0.70 | 0.17 | 0.00 | 61 |
| 1 | 0.40 | 0.17 | 0.52 | 58 |
| 2 | 0.40 | 0.17 | 0.90 | 50 |

String Gel Time (SGT) was measured using a wooden tongue depressor and measuring the time in seconds it takes from the moment of mixing all components (time=0) until string of polymers are observed when touching the foaming mass with the tongue depressor (time=SGT).

TABLE 3

Ambient physical properties of flexible molded foam A, 1 and 2.

| Property | A (Control) | 1 | 2 |
| --- | --- | --- | --- |
| Density (Kg/m3) (ASTM D3574 Test A) | 35 | 35 | 35 |
| Air flow (SCFM) (ASTM D3574 Test G) | 3.8 | 3.8 | 3.9 |
| ILD 25% (ASTM D3574 Test B1) | 166 | 161 | 173 |
| ILD 65% (ASTM D3574 Test B1) | 428 | 415 | 420 |
| ILD Return % (ASTM D3574 Test B1) | 143 | 141 | 151 |
| Tensile strength (kPa) (DIN 53571) | 123 | 123 | 120 |
| Elongation (%) (DIN 53571) | 89 | 76 | 67 |
| 50% Comp. Set (ASTM D3574 Test D) | 5.2 | 6.5 | 16 |

Table 3 shows that when partially replacing control catalyst Dabco® NE1070 with the new catalyst salt "A" then ambient physical properties are comparable with control. Also, partially replacing Dabco® NE1070 with catalyst A does not result in delaying productivity because the string gel time of the process is not affected. Table 4 below shows a comparison of the physical properties after humid ageing following procedure which includes pre-aging samples for 200 hours @ 90° C. and 100% RH wherein the samples are dried before and after this humid age. The detailed procedure is described in "Influence of Non-Fugitive Catalysis On Physical Characteristics of Automotive Polyurethane Molded Foam"; hereby incorporated by reference."

TABLE 4

Humid aged physical properties of flexible molded foam A, 1 and 2.

| Property | A (Control) | 1 | 2 |
| --- | --- | --- | --- |
| Humid aged load loss (HALL) (VW HALLS ISO-3386-1) | −20 | −2.8 | 0.0 |
| HA Tensile strength (kPa) (VW HA-tensile DIN 53571) | 38 | 44 | 61 |
| HA Elongation (%) (VW DIN 53571) | 59 | 61 | 67 |
| 50% HA Comp. Set (VW ASTM D3574-D) | 11 | 11 | 16 |

Thus, significant improvement in physical properties under humid ageing conditions can be seen when using aromatic carboxylic acid salts of tetralkylguanidine. Foam products are more stable to hot humidity when standard amine catalyst are replaced by catalyst "A" as shown by the increase in HA tensile strength and elongation, similar in HA compression set and reduction in humid aged load loss (HALL). Thus, salts of TMG made with aromatic carboxylic acids provide the advantage of yielding flexible molded foam with improved humid aged physical properties.

Example 2

Preparation of Rigid Polyurethane Polymers Made with TMG Salts Using Aromatic and Aliphatic Carboxylic Acids Rigid foam that is typically used in home insulation has been made to evaluate the performance of aromatic salts of tetraalkylguanidine. An example of a typical 2 lb/cuft closed cell rigid foam formulation is shown in Table 5. A typical amine catalyst utilized in this application is Polycat®-30 commercially available form Air Products and Chemicals.

TABLE 5

Rigid spray foam formualtion

| Component | pphp* |
|---|---|
| Polyester Polyol (OH# = 304) | 50 |
| Mannich Polyol (OH# = 465) | 50 |
| Flame Retardant (TCPP) | 21.5 |
| Surfactant (Dabco ® DC193) | 0.25 |
| Catalyst | Varied |
| Water | 3.06 |
| MDI Index | 120 |

*Parts per hundred polyol (wt).

The following components were used:
TCPP—tris-(2-chloropropyl)phosphate

Catalyst 3 is a mixture of tertiary amines containing 88% of tris-(N,N-dimethylaminopropyl)amine, bis-(N,N-dimethylaminopropyl)-N'-methylamine and other related structures together with 12% of a TMG salt of made by combining one mole of phthalic acid with two moles of TMG in PEG-200.

TABLE 6

Foam rate of rise kinetic values for high density spray foam formulation. The kinetic values were measured using using a standard FOMAT instrument equipped with an ultrasonic sensor.

| Parameter | DMEA | Catalyst 3 (12% TMG Salt) |
|---|---|---|
| Use level (pphp) | 2.8 | 2.0 |
| Start time (s) | 11 | 10 |
| Chice time (s) | 19 | 19 |
| Rise time (s) | 29 | 24 |
| Max. Velocity (mm/s) | 22 | 23 |
| Max. Height (mm) | 180 | 167 |
| Final Height (mm) | 178 | 165 |
| Shrinkage | 1.1 | 1.4 |

Result shows that using TMG-salts in spray foam formulations to replace conventional amines results in no significant front end delay as shown by the similar choice time and rise time and that the foam rise velocity is not significantly compromised when the TMG salt is used as a catalyst to partially replace volatile tertiary amines catalysts. Evaluation of emissions from spray foam samples were carried out using VDA 278 analysis which consists on measuring the quantities and identities of chemical emissions taking place at 90° C. and 120° C. TMG was not detected at both temperatures meaning that the salt was fully retained in the polymer framework. Thus, replacing volatile emissive amines with TMG salts resulted in lower emission foam products with the surprising outcome of no delay in reactivity when the acid blocked salt of TMG replaced the non-blocked conventional tertiary amine.

Example 3

Curing Profile Comparison of Elastomeric Polyurethane Polymers Made with TMG Salts Using Aromatic and Aliphatic Carboxylic Acids This example illustrates that TMG salts of aromatic carboxylic acids can be used together with salts of other amines to give polyurethane elastomers with excellent pot-life and curing times. In particular, TMG salts can be used with other amine catalyst salts to replace metal catalysts such as mercury which are normally used as polymerization accelerators in elastomeric applications. Polyurethane elastomers were evaluated using the formulation shown in table 7. Several salts of TMG used in combination with salts of DABCO® DBU (1,8-diazabicyclo[5.4.0]undec-7-ene) were used to compare the curing of the elastomeric material obtained using the formulation of table 7.

TABLE 7

Elastomeric formulation

| Component | pphp |
|---|---|
| Polyether polyol (triol; OH # = 28) | 90.40 |
| 1,4-butane diol | 9.00 |
| Silicon surfactant (Dabco ® DC5000) | 0.1 |
| Molecular sieve powder (3 A) | 0.50 |
| Catalyst | varied |
| Elastomeric type MDI (NCO # = 27.5) | 100 |

A premix was prepared by blending first all of the components shown in Table 7 except for the isocyanate. Thus, the reactive pre-mix contained polyol, 1,4-butane diol, silicon surfactant, molecular sieve and catalyst. The acid blocked catalysts included mixtures of tetramethyl guanidine as well as Dabco®DBUa tertiary amine catalyst commercially available form Air Products and Chemicals. The amine salt mixture could either be prepared by: a) premixing Dabco® DBU with the acid and adding this mixture to the polyol pre-blend containing the tetramethylguanidine salt; b) tetramethyl guanidine was premixed with a carboxylic acid to form a carboxylate salt and this salt was added to the polyol pre-blend containing the corresponding Dabco® DBU salt made with the same carboxylic acid. Table 8 shows the different pot-life and curing time observed for different amine salts made with aromatic carboxylic acids DABCO® BA100. A long pot-life is desired with a good curing time. A long pot life allows for effective mold filling with product rejects minimized. On the other hand, a good curing (shown in table on a scale for 4 to 1; where 4=best and 1=worst) is desired to obtain best physical properties. The result shows that the DBU salt has a very short pot life (undesirable) but a very good cure (desirable). On the other hand, an equimolar amount of TMG salt has a very long pot life (desirable) but very poor cure (undesirable). When combining these two salts in a 1.5/1.0 molar ratio of DBU-salt/TMG-salt a dosing the formulation with an equimolar amount of salt mixture (as shown in table 8) then the best pot-life and curing time were obtained.

TABLE 8

Different amine acid salts made with DABCO ® BA100

| Amine Catalyst | Hg Standard | DBU | TMG | DBN | PC77 | TEDA | TMG/DBU |
|---|---|---|---|---|---|---|---|
| DBU (mmol) | — | 0.567 | — | — | — | — | 0.345 |
| TMG (mmol) | — | — | 0.567 | — | — | — | 0.222 |
| DBN(mmol) | — | — | — | 0.567 | — | — | — |
| PC77(mmol) | — | — | — | — | 0.567 | — | — |
| TEDA (mmol) | — | — | — | — | — | 0.567 | — |
| Total Base (mmol) | — | 0.567 | 0.567 | 0.567 | 0.567 | 0.567 | 0.567 |
| DABCO BA100 (mmol) | — | 0.567 | 0.567 | 0.567 | 0.567 | 0.567 | 0.567 |
| Acid/Base molar ratio | — | 1.0 | 1.0 | 1.0 | 1.0 | 1.0 | 1.0 |
| Potlife | 5'56" | 3'33" | 8'11" | 6'38" | 10'22" | 5'58" | 6'25" |
| Curing | 4 | 2 | 1 | 1 | 1 | 2 | 4 |

Curing test method is based on standard durometer Shore A method (ASTM D2240 type A) over time and assigning to the resulting curves a score form 1=worst to 4=best. Potlife is determined measuring the viscosity (DIN16945) over time using under controlled conditions, at 55° C. using 125-gram of polymerizing material (resin). The test used a Bild Pot Life equipment which rotates a wire hook in the liquid mixture until it thickens to the point where it reaches a predetermined torque level and shuts off. The machine then records the elapsed time. Table 9 shows mixtures of TMG/DBU made with different acids containing aromatic groups and aliphatic substituents as well as the pKa for each acid shown (pKa was measured using conventional methods). The molar ratio of acid to base was 1.0 in all cases. The pKa of DABCO® BA100 is estimated to be approximately 3.8. The best case scenario would correspond to an acid combination with the highest pot-life that can provide the best curing of the polyurethane polymer. In table 9, the best case corresponds to a mixture of salts made with DABCO® DBU and TMG using DABCO® BA100 acid. This combination gave a pot-life of 6"25" and best curing performance (curing=4). Table 8 shows that DABCO®BA100 has approximately the same pKa as formic acid. However, formic acid gave a very short pot-life (1'32') and poor cure (2) so the performance exhibited by DABCO® BA100 can not be explained solely on the basis of acidity. Table 8 also shows the performance of salicylic acid (an aromatic acid) which shows a very long pot life (desirable) but very poor polymer cure (undesirable) making its overall performance undesirable. Salicylic acid is characterized by having a very low pKa (strongly acidic) which may explain its unusual long pot life. The very long pot life may be related to the very strong blocking of the amine resulting in very poor polymer cure. Finally, benzoic acid has a pKa comparable with other aliphatic carboxylic acids such as acetic or 2-EHA but the benzoic acid salt can provide longer pot life than either the acetic or 2-EHA salt. Having an aromatic group attached to the aliphatic chain as in the case of phenylpropionic acid did not result in any improvement in pot-life.

TABLE 9

TMG and DBU salts mixtures made with different acids

| Compound | DBU/TMG | Benzoic | Acetic | Phenyl Propionic | Formic | Salicylic | 2-EHA |
|---|---|---|---|---|---|---|---|
| DBU (mmol) | 0.345 | 0.345 | 0.345 | 0.345 | 0.345 | 0.345 | 0.345 |
| TMG (mmol) | 0.222 | 0.222 | 0.222 | 0.222 | 0.222 | 0.222 | 0.222 |
| Total Base (mmol) | 0.567 | 0.567 | 0.567 | 0.567 | 0.567 | 0.567 | 0.567 |
| BA100 (mmol) | 0.567 | — | — | — | — | — | — |
| Benzoic (mmol) | — | 0.567 | — | — | — | — | — |
| Acetic (mmol) | — | — | 0.567 | — | — | — | — |
| Phenyl Propionic | — | — | — | 0.567 | — | — | — |
| Formic (mmol) | — | — | — | — | 0.567 | — | — |
| Salicylic (mmol) | — | — | — | — | — | 0.567 | — |
| 2-EHA (mmol) | — | — | — | — | — | — | 0.567 |
| Acid/Base molar ratio | 1.0 | 1.0 | 1.0 | 1.0 | 1.0 | 1.0 | 1.0 |

TABLE 9-continued

TMG and DBU salts mixtures made with different acids

| Compound | DBU/TMG | Benzoic | Acetic | Phenyl Propionic | Formic | Salicylic | 2-EHA |
|---|---|---|---|---|---|---|---|
| Potlife | 6'25" | 3'10" | 1'23" | 1'18" | 1'32" | 13'21" | 1'43" |
| Curing | 4 | 3 | 3 | 2 | 2 | 1 | 3 |
| pKa | −3.8 | 4.21 | 4.76 | 4.64 | 3.75 | 2.97 | 4.82 |

Example 4

Curing Profile Comparison of Elastomeric Polyurethane Polymers Made with Aromatic Carboxylic Acids Salts of TMG and TEDA This example illustrates that TMG salts of aromatic carboxylic acids can be used together with salts of TEDA to give polyurethane elastomers with excellent pot-life and curing times. The TMG and TEDA salts combinations can also be used with other amine catalyst salts to replace mercury metal catalysts which are normally used as polymerization accelerators in elastomeric applications. Polyurethane elastomers were evaluated using the formulation shown in table 7.

Table 10 shows the different pot-life and curing time observed for different amine salts A long pot-life is desired with a good curing time. A long pot life allows for effective mold filling with product rejects minimized. On the other hand, a good curing (shown in table on a scale for 4 to 1; where 4=best and 1=worst) is desired to obtain best physical properties.

The result shows that TMG salt combined with TEDA salt (Catalyst A in Table 10) has optimum pot life and cure almost comparable to the standard mercury catalyst. When TMG salt is not present then cure is very poor resulting in undesired physical properties. TMG/TEDA salts can also be used in combinations with other amine salts such as DBU (Catalyst E in Table 10).

TABLE 10

Different amine acid salts made with DABCO ® BA100

| Amine Catalyst | Hg Standard | A | B | C | D | E |
|---|---|---|---|---|---|---|
| DBU (mmol) | — | — | 0.345 | 0.456 | 0.234 | 0.123 |
| TMG (mmol) | — | 0.222 | — | — | 0.222 | 0.222 |
| TEDA (mmol) | — | 0.345 | 0.222 | 0.111 | 0.111 | 0.222 |
| Total Base (mmol) | — | 0.567 | 0.567 | 0.567 | 0.567 | 0.567 |
| DABCO BA100 (mmol) | — | 0.567 | 0.567 | 0.567 | 0.567 | 0.567 |
| Acid/Base molar ratio | — | 1.0 | 1.0 | 1.0 | 1.0 | 1.0 |
| Potlife | 6'15" | 6'11" | 6'20" | 6'26" | 6'26" | 6'18" |
| Curing | 4 | 3 | 1 | 1 | 1 | 3 |

The invention claimed is:

1. A process, comprising:
   providing a pre-mix comprising an aromatic carboxylic acid component comprising phthalic acid;
   contacting a tetraalkylguanidine and at least one amine with the aromatic carboxylic acid component in the pre-mix to form a tetraalkylguanidine salt of aromatic carboxylic acid and an amine salt of the aromatic carboxylic acid wherein the at least one amine comprises at least one member selected from the group consisting of urethane gelling catalyst and urethane blowing catalyst; and,
   adding at least one isocyanate to form a polyurethane composition.

2. The process of claim 1, wherein the acid further comprises one or more of benzoic acid, phenyl-propionic acid, and salicylic acid.

3. The process of claim 1, wherein the pre-mix further comprises a polyol component.

4. The process of claim 3, wherein the pre-mix further comprises at least one member selected from the group consisting of surfactant component, and a crosslinking component.

5. The process of claim 3, wherein the polyol component comprises a polyether polyol and a grafted polyether polyol containing copolymerized styrene and acrylonitrile.

6. The process of claim 3, wherein the polyol component comprises a natural oil or fat polyol.

7. The process of claim 3, wherein the polyol component comprises a polyester polyol.

8. The process of claim 1, wherein the amine salt comprises a tertiary amine salt.

9. The process of claim 8, wherein the tertiary amine salt comprises an isocyanate reactive group.

10. The process of claim 8, wherein the tertiary amine salt is not reactive to an isocyanate.

11. The process of claim 1, further comprising allowing the polyurethane composition to cure.

12. The process of claim 11, wherein the curing of the polyurethane composition forms a molded product.

13. The process of claim 12, wherein the molded product has no amine or acidic emissions.

14. The process of claim 1, wherein temperature dependence of curing is decreased by the contacting of the tetraalkylguanidine with the aromatic carboxylic acid component in the pre-mix to form the tetraalkylguanidine salt of aromatic carboxylic acid.

15. The process of claim 1 wherein the process is substantially free of Hg, Sn, Pb, Bi, Sb, Mn, Fe, Ti, La, Zr, Zn, Co and compounds containing Hg, Sn, Pb, Bi, Sb, Mn, Fe, Ti, La, Zr, Zn.

16. A process of producing a catalyst composition, the process comprising:
   contacting a tetraalkylguanidine with an aromatic carboxylic acid component comprising phthalic acid to form a tetraalkylguanidine salt of aromatic carboxylic acid,
   contacting at least one amine with an acid to form an amine salt wherein the at least one amine comprises at least one member selected from the group consisting of urethane gelling catalyst and urethane blowing catalyst and wherein the at least one amine is not reactive to an isocyanate, and mixing the tetraalkylguanidine salt and the amine salt.

17. A process of producing a catalyst composition, the process comprising:

mixing tetraalkylguanidine and at least one amine wherein the at least one amine comprises at least one member selected from the group consisting of urethane gelling catalyst and urethane blowing catalyst and wherein the at least one amine is not reactive to an isocyanate, and;

adding at least one carboxylic acid comprising phthalic acid to form an amine salt and a tetraalkylguanidine salt of aromatic carboxylic acid.

18. A process, comprising:

providing a pre-mix comprising at least one polyol, at least one aromatic carboxylic acid comprising phthalic acid and an amine salt wherein the amine salt comprises at least one member selected from the group consisting of urethane gelling catalyst salt and urethane blowing catalyst salt;

contacting a tetraalkylguanidine with the pre-mix to form a tetraalkylguanidine salt of aromatic carboxylic acid; and adding at least one isocyanate to form a polyurethane composition.

19. A process, comprising:

providing a pre-mix consisting essentially of at least one polyol, at least one tetraalkylguanidine salt of phthalic acid and at least one amine salt wherein the amine salt comprises at least one member selected from the group consisting of urethane gelling catalyst salt and urethane blowing catalyst salt, and;

adding at least one isocyanate to the pre-mix to form a polyurethane composition.

20. The process of claim 19 wherein the process further comprises introducing the polyurethane composition to a mold; and removing an elastomeric polyurethane product from the mold.

21. The process of claim 19 wherein the polyol is a polyether triol polyol, the amine salt is an aromatic carboxylic acid salt of 1,8-diazabicyclo[5.4.0]undec-7-ene and the isocyanate comprises 4, 4'-diphenylmethane diisocyanate.

22. The process of claim 19 wherein the amine salt is a salt of at least one tertiary amine and the aromatic carboxylic acid.

23. The process of claim 19 wherein the pre-mix further includes at least one member selected from the group consisting of ethylene glycol, diethylene glycol and polyethylene glycol.

24. The process of claim 23 wherein said member is polyethylene glycol.

25. The process of claim 19 wherein the amine salt is an aromatic carboxylic acid salt of 1,8-diazabicyclo[5.4.0]undec-7-ene.

26. The process of claim 19 wherein the amine salt is an aromatic carboxylic acid salt of triethylene diamine.

27. The process of claim 26 further including an aromatic carboxylic acid salt of 1,8-diazabicyclo[5.4.0]undec-7-ene.

* * * * *